(12) United States Patent
Poston et al.

(10) Patent No.: US 6,506,385 B1
(45) Date of Patent: Jan. 14, 2003

(54) LIVE VACCINES AND METHODS OF TREATMENT THEREWITH

(75) Inventors: Rebecca M. Poston, Hillsborough, NC (US); Paul A. Johnston, Durham, NC (US); Vivian W. Doelling, Cary, NC (US); Brian D. Johnson, Cary, NC (US)

(73) Assignee: Embrex, Inc., Research Triangle Park, NC (US)

( * ) Notice: Subject to any disclaimer, the term of this patent is extended or adjusted under 35 U.S.C. 154(b) by 0 days.

(21) Appl. No.: 09/292,730

(22) Filed: Apr. 15, 1999

(Under 37 CFR 1.47)

Related U.S. Application Data

(60) Provisional application No. 60/082,196, filed on Apr. 17, 1998.

(51) Int. Cl.$^7$ .............. A61K 38/21; A61K 39/00; A61K 39/12; A61K 45/00; C12Q 1/70

(52) U.S. Cl. .............. 424/184.1; 424/85.4; 424/204.1; 424/214.1; 424/281.1; 435/5

(58) Field of Search .............. 119/6.8; 424/9.2, 424/85.4, 184.1, 204.1, 214.1, 281.1, 816; 435/5; 536/23.52

(56) References Cited

U.S. PATENT DOCUMENTS

| | | | |
|---|---|---|---|
| 4,053,583 A | 10/1977 | Gits et al. | 424/90 |
| 4,689,224 A | 8/1987 | Bull et al. | 424/89 |
| 4,820,514 A | 4/1989 | Cummins | 424/85.4 |
| 5,334,379 A | 8/1994 | Pillai et al. | 424/85.2 |
| 5,378,457 A | 1/1995 | Paoletti et al. | 424/205.1 |
| 5,397,568 A | 3/1995 | Whitfill et al. | 424/178.1 |
| 5,529,777 A | 6/1996 | Andrianov et al. | 424/184.1 |
| 5,562,910 A | 10/1996 | Daynes et al. | 424/278.1 |
| 5,605,827 A | 2/1997 | Jackwood et al. | 435/235.1 |
| 5,698,530 A | 12/1997 | Schlom et al. | 514/44 |
| 5,705,151 A | 1/1998 | Dow et al. | 424/93.21 |
| 5,723,127 A | 3/1998 | Scott et al. | 424/184.1 |
| 5,723,283 A | 3/1998 | Classen | 435/4 |
| 5,728,385 A | 3/1998 | Classen | 424/201.1 |
| 5,885,567 A | 3/1999 | Sekellick et al. | 424/85.4 |
| 5,906,826 A | 5/1999 | Emery et al. | 424/422 |
| 5,910,304 A | 6/1999 | Cummins | 424/85.7 |
| 5,928,649 A | 7/1999 | Daley et al. | 424/211.1 |

FOREIGN PATENT DOCUMENTS

| | | | |
|---|---|---|---|
| EP | 0 609 739 A1 | 8/1994 | A61K/39/39 |
| WO | WO 87/04076 | 7/1987 | A61K/45/02 |
| WO | WO 95/11302 | 4/1995 | C12N/15/20 |
| WO | WO 96/05291 | 2/1996 | C12N/5/10 |
| WO | WO 96/27666 | 9/1996 | C12N/15/20 |
| WO | WO 98/37216 | 8/1998 | C12N/15/85 |

OTHER PUBLICATIONS

Sharma et al. 1996. Effect of cytokines on the immune system following in ovo administration. JAVMA. vol. 209, No. 2, p. 398, Session A of Poultry Medicine.*

Gildersleeve 1993. In ovo vaccination update. Proc. Nat. Meet. Poultry Health–Process. 28 Meeting, pp. 6–10.*

Sekellick et al. 1994. Chicken interferon gene: cloning, expression, and analysis. Journal of interferon research. vol. 14, pp. 71–79.*

Dhillon et al. 1994. Newcastle recombinant vaccine protects chickens with maternal antibodies.Proceedings of the forty–third western poultry disease conference. Feb. 27–Mar. 1.*

Reddy et al. 1996. Protective efficacy of a recombinant herpesvirus of turkeys as an in ovo vaccine against Newcastle and Marek's diseases in specific–pathogen–free chickens. Vaccine. vol. 14, No. 6, pp. 469–477.*

Karaca et al. 1998. Rec. fowlpox viruses coexpressing chicken type 1 INF & Newcastle disease virus HN&F genes: influence of INF on protective efficacy and humoral responses of chickens following in ovo or posthatch administration of rec. viruses. Vaccine.*

Baer et al.; Successful Prophylaxis against Rabies in Mice and Rhesus Monkeys: The Interferon System and Vaccine, *The Journal of Infectious Diseases*, vol. 136, No. 2, pp. 286–290 (1977).

Cao et al.; Enhancement of the protective effect of inactivated influenza virus vaccine by cytokines, Dept. of Microbiology, Kyoto Prefectural University of Medicine, Kamigyo–ku, Kyoto 602, Japan (1991).

Dhillon et al.; Newcastle Recombinant Vaccine Protects Chickens with Maternal Antibodies, Proceedings of the 43$^{rd}$ Western Poultry Disease Conference, Sacramento, CA, p. 108, (1994).

(List continued on next page.)

*Primary Examiner*—James Housel
*Assistant Examiner*—Shanon A. Foley
(74) *Attorney, Agent, or Firm*—Myers Bigel Sibley & Sajovec, P.A.

(57) ABSTRACT

Disclosed herein are methods and pharmaceutical formulations for administering vaccines to birds. In preferred embodiments, the invention provides methods of administering live pathogenic virus vaccines to birds in ovo, more preferably, during the last quarter of in ovo incubation. Interferon, more preferably, Type I interferon, may be advantageously administered in conjunction with live virus vaccines to decrease the pathogenicity thereof. Interferon must be provided at doses sufficient to protect against pathogenicity of the live vaccine, but not at doses so high as to prevent the host from mounting an active immune response. Further provided are pharmaceutical formulations comprising effective doses of live vaccine and interferon. Finally, the present invention provides methods of administering interferon together with live vaccines to young avians to effectively overcome the interfering effects of maternal antibodies.

43 Claims, 11 Drawing Sheets-

OTHER PUBLICATIONS

Gough et al.; Further studies on the adjuvant effect of an interferon inducer (BRL 5907) on Newcastle disease and avian influenza inactivated vaccines, *Research in Veterinary Science*, 19, 185–188 (1975).

Heath et al.; Cytokines as immunological adjuvants, *Vaccine*, vol. 10, Issue 7 (1992).

Karaca, et al.; Immunomodulating Effects of Avian Recombinant Cytokines, *JAVMA*, vol. 209, No. 2, (1996) (Abstract).

Lin et al.; Present Status of the Use of Cytokines as Adjuvants with Vaccines to Protect Against Infectious Diseases, *Clinical Infectious Diseases*, 21:1439–49 (1995).

Moreno et al.; Further Studies on Rabies Postexposure Prophylaxis in Mice: a Comparison of Vaccine with Interferon and Vaccine, *J. gen. Virol.* 42, 219–222 (1979).

Ramshaw et al.; Cytokine expression by recombinant viruses—a new vaccine strategy, *Tibtech*, 10:425–426 (1992).

Sharma et al.; Effect Of Recombinant Interferon On Viral Immunosuppression in Chickens, Proceedings of the $45^{th}$ Western Poultry Disease Conference, Cancun, Mexico, (1996).

Van Oirschot et al.; Maternal Antibodies against Equine Influenza Virus in Foals and their Interference with Vaccination, *J. Vet. Med.* B 38, 391–396 (1991).

Watkins et al.; The Effect of *In Ovo* Oocyst or Sporocyst Inoculation on Response to Subsequent Coccidial Challenge, *Poultry Science*, 74: 1597–1602 (1995).

Werenne et al.; Antiviral Effect of Bacterially Produced Human Interferon (Hu–IFN$\alpha_2$) Against Experimental Vaccinia Infection in Calves, *Journal Of Interferon Research*, 5:129–136 (1985).

Lowenthal et al.; *Coadministration of IFN–$\gamma$ Enhances Antibody Responses in Chickens*, Journal of Interferon and Cytokine Research 18:617–622 (1998).

International Search Report, PCT/US99/08530, Date of Mailing: Nov. 26, 1999.

* cited by examiner

Figure 10.

LIVE VACCINES AND METHODS OF TREATMENT THEREWITH

RELATED APPLICATION INFORMATION

This application claims the benefit of U.S. Provisional Application No. 60/082,196 filed Apr. 17, 1998, which is incorporated by reference herein in its entirety.

FIELD OF THE INVENTION

The present invention relates to methods for protecting avians against disease, in particular methods of administering vaccines to avians.

BACKGROUND OF THE INVENTION

Newcastle disease (ND) causes global economic losses for the poultry industry in the range of 40 million dollars annually. The disease is caused by several different RNA viruses from the Paramyxoviridae family and symptoms range from subclinical disease to high mortality. Although vaccination programs can control ND, there are still problems due to adverse vaccine reactions and requirements for multiple vaccine administrations.

Chicks raised in the commercial poultry industry typically are vaccinated against multiple diseases. In the past, immunization for NDV generally occurred at day one and day fourteen post-hatch. More recently, in ovo injection devices have automated immunization, allowing treatment of the embryos prior to hatch. However, thus far, there has been little success with in ovo administration of live viral vaccines without a high incidence of embryo mortality. Use of a virulent NDV or other viral vaccine strain capable of producing a protective immune response with one in ovo administration would be highly advantageous. However, in ovo NDV live virus vaccination is usually toxic to the embryo, and birds that do hatch from in ovo vaccinated eggs exhibit high early mortality. Ahmad & Sharma, (1993) *Avian Diseases* 37:485.

Accordingly, there remains a need in the art for safe and efficacious methods of administering live pathogenic virus vaccines to birds in ovo.

SUMMARY OF THE INVENTION

The present invention is based on the discovery that interferon can be administered in conjunction with vaccines to decrease the pathogenicity thereof. In particular, interferons are effective in decreasing the pathogenic effects of live vaccines in embryonic birds. Accordingly, the present invention provides methods and pharmaceutical formulations for administering live pathogenic vaccines, preferably live pathogenic virus vaccines, to birds in ovo. The dose of interferon must be sufficient to protect the subject from the pathogenic effects of the live vaccines, but should not be so high as to prevent infection by the vaccine.

In addition, the present investigations have led to the discovery that administration of interferon in conjunction with vaccines to birds in ovo and hatchlings can overcome the inactivating (i. e., neutralizing) effects of maternal antibodies. It is well-known in the art that maternally-transmitted antibodies interfere with the efficacy of early vaccination programs in young birds. Accordingly, the present invention provides methods and pharmaceutical formulations for effectively vaccinating avian embryos and young maternal antibody positive avians.

In one embodiment, the present invention provides a method of producing protective immunity against a viral disease in an avian subject, comprising: (a) administering to an avian subject in ovo a composition comprising a vaccine comprising a live pathogenic virus; and (b) administering to the avian subject in ovo a composition comprising interferon; wherein the live pathogenic virus is administered in an amount effective to produce an immune response in the avian subject; and wherein the interferon is administered in an amount effective to (1) protect the avian subject from pathology that would occur in the absence of the interferon due to the administration of the vaccine, and (2) allow the production of a protective immune response in the avian subject.

As a further aspect, the present invention provides a method of producing protective immunity against Newcastle disease in a chicken, comprising: (a) administering to a chicken during the last half of in ovo incubation a composition comprising a vaccine comprising a live pathogenic Newcastle disease virus; and (b) administering to a chicken during the last half of in ovo incubation a composition comprising a Type I interferon; wherein the live pathogenic virus is administered in an amount effective to produce an immune response in the chicken; and wherein the Type I interferon is administered in an amount effective to (1) protect the chicken from pathology that would occur in the absence of the Type I interferon due to the administration of the vaccine, and (2) allow the production of a protective immune response in the chicken.

As a further embodiment, the present invention provides a method of reducing mortality from the administration of a live vaccine virus in ovo to an avian subject, comprising: (a) administering to an avian subject in ovo a composition comprising a vaccine comprising a live vaccine virus; and (b) administering to the avian subject in ovo a composition comprising interferon; wherein the live vaccine virus is administered in an amount effective to produce an immune response in the avian subject; and wherein the interferon is administered in an amount effective to (1) protect the avian subject from pathology that would occur in the absence of the interferon due to the administration of the vaccine, and (2) allow the production of a protective immune response in the avian subject.

As still a further aspect, the present invention provides a method of reducing disease from the administration of a live vaccine virus in ovo to an avian subject, comprising: (a) administering to an avian subject in ovo a composition comprising a vaccine comprising a live vaccine virus; and (b) administering to the avian subject in ovo a composition comprising interferon; wherein the live vaccine virus is administered in an amount effective to produce an immune response in the avian subject; and wherein the interferon is administered in an amount effective to (1) protect the avian subject from pathology that would occur in the absence of the interferon due to the administration of the vaccine, and (2) allow the production of a protective immune response in the avian subject.

As yet a further aspect, the present invention provides a method of producing protective immunity against a viral disease in an avian subject, the method comprising administering to an avian subject during the last quarter of in ovo incubation a composition comprising a vaccine comprising a live pathogenic virus and interferon, wherein the live pathogenic virus is administered in an amount effective to produce an immune response in the avian subject; and wherein the interferon is administered in an amount effective to (1) protect the avian subject from pathology that would occur in the absence of the interferon due to the administration of the vaccine, and (2) allow the production of a protective immune response in the avian subject.

Pharmaceutical formulations comprising a composition comprising a vaccine comprising a live pathogenic virus and interferon in a pharmaceutically-acceptable carrier are also an aspect of the invention.

As yet a further aspect, the present invention provides a method of producing protective immunity against a viral disease in an avian subject, comprising: (a) administering to an avian subject during the first month post-hatch a composition comprising a vaccine comprising a live pathogenic virus; and (b) administering to the avian subject during the first month post-hatch a composition comprising interferon; wherein the live pathogenic virus is administered in an amount effective to produce an immune response in the avian subject; and wherein the interferon is administered in an amount effective to (1) protect the avian subject from pathology that would occur in the absence of the interferon due to the administration of the vaccine, and (2) allow the production of a protective immune response in the avian subject.

These and other aspects of the present invention will be set forth in more detail in the description of the invention below.

BRIEF DESCRIPTION OF THE DRAWINGS

FIG. 10 is a graphical representation of the effects of IFN-I co-administration with NDV vaccination in ovo on 7-day post-hatch survivability of SPF chicken embryos. Embryonic day 18 eggs were co-administered 0, 5, 15, 30 or 45 µg IFN-I per egg together with 10 $EID_{50}$ NDV vaccine, and survivability for each treatment group was monitored for 7 days following hatch. One treatment group only received PBS (positive control). There were 60 eggs per treatment group.

DETAILED DESCRIPTION OF THE INVENTION

Figure 1:
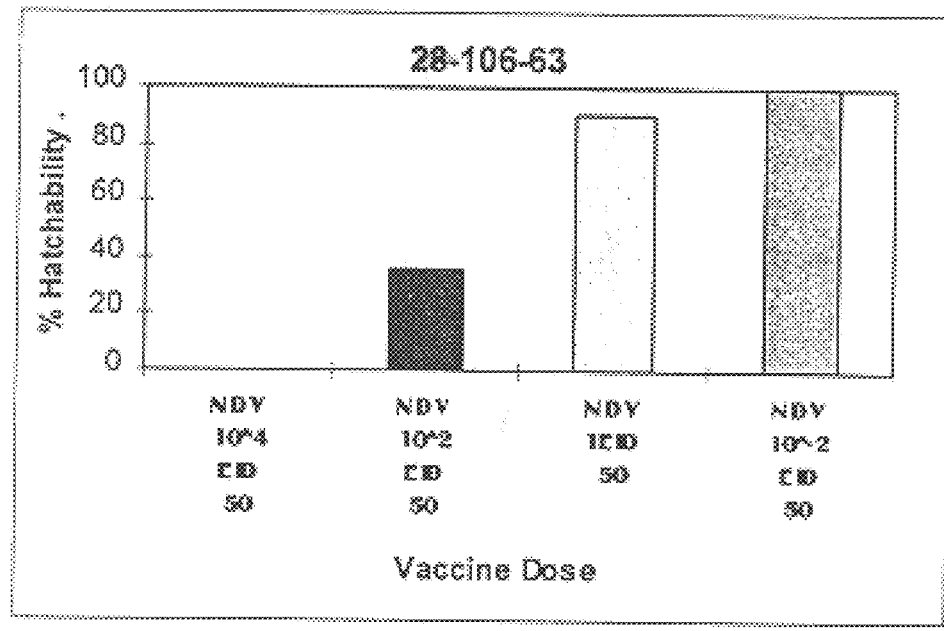
FIG. 1 is a graphical representation of the effects of in ovo NDV vaccine dose on hatchability of SPF chicken embryos. Embryonic day 18 eggs were administered either PBS or a $10^4$, $10^2$, 1 or $10^{-2}$ $EID_{50}$ dose of NDV vaccine, and hatchability of each treatment group was monitored. There were 40 eggs per treatment group.

The present invention provides methods and pharmaceutical formulations for administering live virus vaccines to birds in ovo. The invention is based, in part, upon the discovery that administration of interferon (IFN), in particular Type I interferon (IFN-I), can protect birds from the pathology and mortality associated with administration of live virus vaccines to bird embryos. Prior to the present investigations, vaccines against Marek's Disease and bursal Disease were the only live viral vaccines that could be administered in ovo without a high incidence of embryo mortality. The invention is further based on the discovery that administration of IFN, in particular IFN-I, in conjunction with vaccination with live virus vaccines pre- or post-hatch provides a means to effectively vaccinate birds in the presence of interfering maternal antibodies. Furthermore, the present invention provides pharmaceutical formulations and methods for administering live virus vaccines (i.e., to produce active immunity against the virus) in conjunction with IFN to birds in ovo, without causing substantial disease or death (either pre- or post-hatch) among the vaccinated birds.

A. Interferon

Interferon for use in the present invention can be IFN-I and/or IFN-II, with IFN-I being preferred. IFN-I is a family of closely-related proteins that are produced by leucocytes ($\alpha$ subtypes), fibroblasts ($\beta$ subtypes), lymphocytes (IFN$\omega$), and ruminant embryos (IFN$\tau$). Robert J. Donnelly, The Type I ($\alpha/\beta/\omega/\tau$) Interferon Family, in *Guidebook to Cytokines and Their Receptors* 111 (Nicos A. Nicola ed., 1994). The term "interferon" as used herein encompasses biologically-active IFN analogs and derivatives (e.g., can protect an avian subject from the pathogenic effects of a live vaccine, as described herein, or alternatively, possesses any other known biological action of IFN), as well as biologically-active truncated IFN molecules, as are known by those of skill in the art. The IFN can be recombinant or purified from natural sources, with recombinant being preferred. Additionally, the IFN can be purified by any method known in the art. Finally, the IFN can be from any species of origin, including avian and mammalian IFNs, for example, chicken, turkey, murine, human, and bovine IFN. Avian IFNs are preferred for administration to avian subjects, with chicken and turkey IFN being more preferred, and chicken IFN being most preferred. Mammalian IFNs are preferred for administration to mammalian subjects, with human, bovine, and murine IFNs being more preferred. In general, it is preferred to administer IFN derived from the same species as the subject.

According to the present invention, IFN is incorporated in pharmaceutical formulations and administered in an amount effective to reduce (i.e., ameliorate, delay, diminish, and/or decrease) the pathogenic effects (e.g., disease, mortality, etc.) caused to the avian embryo by the in ovo administration of the live pathogenic virus vaccine, without blocking the production of a protective immune response in the bird. By "reduce", it is not meant that there be no detrimental effects from the virus vaccine. The IFN ameliorates the pathogenic effects of the virus vaccine, such that the benefits of vaccination outweigh the detriments. Alternatively stated, the IFN will significantly reduce (i.e., ameliorate, delay, diminish, and/or decrease) the pathogenic effects normally seen after administration of the virus vaccine in the absence of IFN.

While not wishing to be held to any particular theory of the invention, it appears that effective doses of IFN protect the bird against the pathogenic effects of the virus, but allow production of an active and protective immune response. High doses of IFN may be unsuitable in the present methods and pharmaceutical formulations, as they may reduce or even block viral replication such that a protective immune response is not induced. Thus, according to the present invention, the dose of IFN should not be so high that a protective immune response is prevented. It appears that there is a "window" of effective IFN doses for carrying out the present invention. Alternatively, it appears that there is an effective ratio of IFN to vaccine, with too low or too high an IFN dose, as compared with the dose of vaccine, being detrimental. Ranges of IFN outside the effective window, alternatively ratios of vaccine to virus outside of the effective range, will impede, rather than increase, vaccine efficacy.

This critical window for interferon dosage has not previously been appreciated by the art. For example, U.S. Pat. No. 4,820,514 to Cummins describes a method of vaccinating feeder cattle by oral administration of an infectious bovine rhinotracheitis virus vaccine in conjunction with IFN$\alpha$. However, Cummins fails to disclose that there is a window of effective IFN doses, or that ratios of vaccine to IFN outside of the effective range will impede, rather than increase, vaccine efficacy.

The terms "protective immunity" or "protective immune response," as used herein, are intended to mean that the host bird mounts an active immune response to the virus vaccine, such that upon subsequent exposure to the virus or a virulent viral challenge, the bird is able to combat the infection. Thus, a protective immune response will decrease the incidence of morbidity and mortality from subsequent exposure to the virus among host birds. It is possible that with co-administration of IFN there will be a reduction in the immune response to the virus, but this diminishment will not be so severe that the effectiveness of the vaccine to protect the bird against future virus exposure is substantially or totally eliminated. Those skilled in the art will understand that in a commercial poultry setting, the production of a protective immune response may be assessed by evaluating the effects of vaccination on the flock as a whole, e.g., there may still be morbidity and mortality in a minority of vaccinated birds.

By "active immune response", it is meant any level of protection from subsequent exposure to the virus or virus antigens which is of some benefit in a population of subjects, whether in the form of decreased mortality, decreased lesions, improved feed conversion ratios, or the reduction of any other detrimental effect of the disease, and the like, regardless of whether the protection is partial or complete. An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development cell-mediated reactivity, or both." Herbert B. Herscowitz, Immunophysiology. Cell Function and Cellular Interactions in Antibody Formation, in *Immonology: Basic Processes* 117 (Joseph A. Bellanti ed., 1985). Alternatively stated, an active immune response is mounted by the host after exposure to immunogens by infection, or as in the present case, by vaccination. Active immunity can be contrasted with passive immunity, which is acquired through the "transfer of preformed substances (antibody, transfer factor, thymic graft, interleukin-2) from an actively immunized host to a non-immune host." Id.

With respect to the degree of protection provided by the interferon, the quantity of interferon administered in combination with the live virus in the vaccine need not be sufficient to provide complete protection from the pathogenic effects of the virus, as long as the detrimental response produced by the virus is reduced to a level at which the benefits of the immune response produced outweigh any harm resulting from the vaccination. The IFN can be administered in doses as low as 0.01, 0.1, 0.5, 1, 2.5, 5, 10 or 15 µg/egg, or less, and in doses as high as 20, 25, 30, 40, 50, 60, 70, 80, 100, 150, or even 200 µg/egg, or more. Pharmaceutical formulations are compounded to include these quantities of IFN per dose.

B. Virus Vaccines

The present invention is advantageously employed with live virus vaccines, preferably, vaccines containing live pathogenic viruses, i.e., virus vaccines capable of causing disease or death in the subject if not for the co-administration of IFN-I or IFN-II, preferably IFN-I. The pathogenicity of the virus may be inherent in the virus itself or due to the susceptibility of the subject to be treated (e.g., birds in ovo). Alternatively, the term "pathogenic", as used to describe virus vaccines herein, means that the harm caused subjects by administration of the virus vaccine outweighs any benefit which would result therefrom. In general, more strongly pathogenic viruses (i.e., less attenuated viruses and/or non-attenuated viruses) are preferred. The virus vaccine should be capable of producing an active immune response thereto in the avian subject being treated.

As used herein, the term "live virus" refers to a virus that retains the ability of infecting an appropriate subject (as opposed to inactivated or subunit vaccines). Furthermore, as used herein, a "vaccine virus" refers to a virus that is capable of conferring protective immunity in appropriate subjects, with acceptable associated mortality and morbidity. The term "live pathogenic virus" as used herein is intended to exclude those live viruses (typically non-pathogenic live viruses) that have been engineered to express an antigen from a pathogenic virus or otherwise engineered to confer pathogenicity (e.g., engineered to express a toxin). Vaccine viruses include, e.g., commercial live virus vaccines for use in avians post-hatch. However, it must be noted that vaccine viruses that are safe for use in post-hatch avians may be associated with unacceptable mortality and morbidity when used in ovo.

According to the present invention, the live vaccine virus is administered in an amount per unit dose sufficient to evoke an active and protective immune response to the virus in the subject to be treated. It has been discovered in the course of the investigations described herein that administration of live vaccine virus in conjunction with IFN reduces the amount of virus that must be included in the vaccine formulations to achieve a protective immune response. As little as 10, 100, 1000, or even 10,000 fold lower doses of virus are required to induce an immune response when the virus vaccine is administered in conjunction with IFN according to the present invention as compared with post-hatch virus doses in the absence of IFN. The exact dose of virus to be administered in the vaccine is not critical except that the dose must be effective to engender an active and protective immune response by the bird. In general, depending on the inoculum administered, the site and manner of administration, the species, age and condition of the subject, etc., the virus dose will range from a $10^{-2}$ to $10^7$ EID$_{50}$ dose of virus (i.e, Embryo Infectious Dose$_{50}$—the dose at which 50% of vaccinated embryos are infected), more preferably a $10^{-1}$ to $10^6$ EID$_{50}$ dose of virus, yet more preferably a $10^1$ to $10^3$ EID$_{50}$ dose of virus, most preferably a $10^2$ EID$_{50}$ dose of virus. Pharmaceutical formulations are compounded to include these quantities of virus per dose.

Live viruses that may be included in vaccines to be used according to the present invention encompass any infectious avian virus, in particular live pathogenic viruses (as defined above). Exemplary infectious avian viruses include, but are not limited to, rous sarcoma virus, Newcastle disease virus, infectious bursal disease virus, infectious bronchitis virus, avian infectious laryngeotracheitis virus, turkey rhinotracheitis virus, avian leukosis virus, Marek's disease virus, chicken anemia virus, avian influenza virus, Paramyxovirus group 2-9 viruses (PMV 2-9), avipox, herpes virus of turkeys, duck enteritis virus, Pacheco's disease virus, duck hepatitis virus, adenovirus, parvovirus, polyomavirus, pneumovirus, orthomyxovirus, coranovirus, reovirus, rotavirus, bimavirus, enterovirus, oncornavirus, arbovirus, flavovirus, and astrovirus, with Newcastle disease virus being preferred.

In general, in reference to the viruses specifically enumerated above, it is intended that the present invention encompass all strains of such viruses. Viruses and strains thereof are well known in the art. See, e.g., AMERICAN ASSOCIATION OF AVIAN PATHOLOGISTS, *A Laboratory Manual for the Isolation and Identification of Pathogens* (3d. ed. 1989).

The term "infectious bursal disease virus" (IBDV), as used herein, encompasses all strains of IBDV. Exemplary are the Bursal Disease Vaccine, Lukert strain, live virus, which is obtained from either Vineland Laboratories (Vineland, N.J.) or Salsbury Laboratories (Charles City, Iowa), the Bursal Disease Virulent Challenge Virus, which is obtained from the United States Department of Agriculture in Ames, Iowa (original isolate from S. A. Edgar), and Infectious Bursal Disease Virus strain VR2161, disclosed in U.S. Pat. No. 4,824,668 to Melchior and Melson.

The term "rous sarcoma virus" (RSV), as used herein encompasses all strains of RSV. RSV has been comprehensively studied since its discovery early this century. See generally 1 RNA Tumor Viruses: Molecular Biology of Tumor Viruses 59–61 (R. Weiss et al., eds., 2d ed. 1984). Moloney (*J. Nat. Cancer Inst.* 16:877) reports the development of standard lots of the virus for use in quantitative investigations. See also, U.S. Pat. No. 3,326,767 to Holper and Kiggins. Numerous RSV strains are listed in the American Type Culture Collection Catalogue of Animal and Plant Viruses, Chlamydiae, Rickettsiae and Virus Antisera ($5^{th}$ ed. 1986), at pages 110–112.

The term "infectious bronchitis virus" (IBV), as used herein, encompasses all strains of IBV. Exemplary strains include, but are not limited to Mass. 41 Strain, Arkansas 99 Strain, Connecticut A5968, and Michigan State University Repository Code 42 Strain, all available from American Type Culture Collection (Rockville, Md.).

The term "adenovirus," as used herein, encompasses all strains of adenoviruses. Adenoviruses infect most species of turkeys and include Group I adenoviruses, hemorrhagic enteritis viruses, marble spleen disease viruses, the splenomegaly virus of chickens, and egg-drop syndrome-76 (EDS-76) virus.

Finally, the term "Newcastle Disease virus", also known as "Type I Paramyxovirus" or "PMV-1", as used herein, encompasses all strains of Newcastle Disease virus.

C. Vaccination of Birds in ovo with Live Pathogenic Virus Vaccines

Thus, in the most preferred embodiments, the present invention provides a method of in ovo vaccination of avians by the co-administration of IFN, preferably IFN-I, and a live pathogenic virus. The amount of IFN administered will vary depending on the amount and type of virus being administered, and the developmental stage (e.g., embryonic age) and species of the avian being treated. However, the amount of IFN is sufficient to reduce the pathogenic effects of the virus that would otherwise occur in the absence of IFN. The amount of IFN is insufficient, however, to prevent the treated avian from mounting a protective immune response. Those skilled in the art will appreciate that other factors can be co-administered with the vaccine virus and the IFN, for example, to enhance the immune response to the virus and/or the protective effects of the IFN.

It will also be apparent to those skilled in the art that, when treating a plurality of avians (such as in commercial poultry production), the reduction in pathogenic effects may be assessed by evaluating the effects of vaccination on the flock as a whole. In other words, an effective amount of IFN used in conjunction with a pathogenic virus to immunize a plurality of birds may still cause morbidity or mortality in a minority of birds.

D. Subjects, Modes of Administration, and Pharmaceutical Formulations

The term "avian" and "avian subjects," as used herein, is intended to include males and females of any avian species, but is primarily intended to encompass poultry which are commercially raised for eggs, meat or as pets. Accordingly, the terms "avian" and "avian subject" are particularly intended to encompass chickens, turkeys, ducks, geese, quail, pheasant, parakeets, parrots, and the like. Chickens and turkeys are the preferred avian subjects, with chickens being most preferred. The avian subject may be a hatched bird, including newly-hatched (i.e., about the first three days after hatch), adolescent, and adult birds.

Avian subjects may be administered interferon and vaccines of the present invention by any suitable means. Exemplary means are oral administration (e.g., in the feed or drinking water), intramuscular injection, subcutaneous injection, intravenous injection, intra-abdominal injection, eye drop, or nasal spray. Birds may also be administered vaccines in a spray cabinet, i.e., a cabinet in which the birds are placed and exposed to a vapor containing vaccine, or by course spray. When administering the inventive vaccines to birds post-hatch, administration by subcutaneous injection or spray cabinet are preferred. Birds may also be administered the vaccine in ovo, as described in U.S. Pat. No. 4,458,630 to Sharma. In ovo administration of vaccine is most preferred. As a practical matter, it may be desirable to administer compositions including two or more vaccines to the subject at the same time.

The in ovo administration of vaccine, as described hereinabove, involves the administration of the vaccine to the avian embryo while contained in the egg. The vaccine may be administered to any suitable compartment of the egg (e.g., allantois, yolk sac, amnion, air cell, or into the avian embryo itself), as would apparent to one skilled in the art. Preferably, the vaccine is administered to the amnion. Eggs administered the vaccines of the present invention are fertile eggs which are preferably in the last half, more preferably the last quarter, of incubation. Chicken eggs are treated on about the twelfth to twentieth day of incubation, more preferably the fifteenth to nineteenth day of incubation, and are most preferably treated on about the eighteenth day of incubation (the eighteenth day of embryonic development). Turkey eggs are preferably treated on about the fourteenth to twenty-sixth day of incubation, more preferably on about the twenty-first to twenty-seventh day of incubation, most preferably on about the twenty-fifth day of incubation. Those skilled in the art will appreciate that the present invention can be carried out at any predetermined time in ovo, as long as the embryo is able to mount an immune response to the virus vaccine, and the IFN is able to protect the bird against the pathogenic effects of the virus.

In preferred embodiments of the invention, chicken eggs are administered a live pathogenic Newcastle disease virus vaccine and a composition containing IFN-I during the last half of in ovo incubation (preferably the last quarter of in ovo incubation). The two administration steps may be, but need not be, concurrent.

The IFN and vaccine can be administered concurrently, but concurrent administration is not necessary. "Concurrently" or "concurrent administration" is used herein to mean administration within minutes of the same time, not necessarily at the same precise moment. Concurrent administration may be carried out by mixing IFN and vaccine prior to inoculation, or by simultaneous injection of the two compounds, at the same or at different sites. Alternatively, the IFN can be injected before the vaccine (even days before) to "prime" the bird prior to inoculation with the vaccine. As a further alternative, the IFN can be administered after the vaccine has had the opportunity to infect the bird. For ease of handling in a commercial hatchery, it is preferable to administer the IFN and virus vaccine concurrently.

If IFN is to be administered to animals concurrently with the administration of the vaccine, the two can be administered separately or mixed together. If IFN and vaccine are mixed together prior to administration, the vaccine formulation can be the same as standard vaccine formulations (which include a suspension of virus suitable for inducing immunity to an infectious disease), with the addition of the necessary amount of a biologically active IFN. Such vaccine formulations are well known to those skilled in the art. Such formulations can include pharmaceutically acceptable carriers, such as saline or phosphate-buffered saline (PBS).

Eggs may be administered the vaccines and IFN by any means which transports the compound through the shell. The preferred method of administration is, however, by injection. The substance may be placed within an extraembryonic compartment of the egg (e.g., yolk sac, amnion, allantois, air cell) or within the embryo itself. The site of injection is preferably within the region defined by the amnion, including the amniotic fluid and the embryo itself. By the beginning of the fourth quarter of incubation, the amnion is sufficiently enlarged that penetration thereof is assured nearly all of the time when the injection is made from the center of the large end of the egg along the longitudinal axis.

The mechanism of egg injection is not critical, but it is preferred that the method not unduly damage the tissues and organs of the embryo or the extraembryonic membranes surrounding it so that the treatment will not decrease hatch rate. A hypodermic syringe fitted with a needle of about 18 to 22 gauge is suitable for the purpose. To inject into the air cell, the needle need only be inserted into the egg by about two millimeters. A one-inch needle, when fully inserted from the center of the large end of the egg, will penetrate the shell, the outer and inner shell membranes enclosing the air cell, and the amnion. Depending on the precise stage of development and position of the embryo, a needle of this length will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

It is envisioned that a high-speed automated egg injection system for avian embryos will be particularly suitable for practicing the present invention. Numerous such devices are available, exemplary being those disclosed in U.S. Pat. Nos. 4,681,063 and 4,903,635 to Hebrank and U.S. Pat. Nos. 4,040,388, 4,469,047, and 4,593,646 to Miller. All such devices, as adapted for practicing the present invention, comprise an injector containing the vaccine described herein, with the injector positioned to inject an egg carried by the apparatus with the vaccine. Other features of the apparatus are discussed above. In addition, if desired, a sealing apparatus operatively associated with the injection apparatus may be provided for sealing the hole in the egg after injection thereof.

A pharmaceutical formulation of the present invention is made by mixing the IFN, preferably IFN-I, with a vaccine in a pharmaceutically acceptable carrier. Pharmaceutical formulations of the present invention preferably comprise the vaccine and the IFN in a lyophilized form or in a pharmaceutically acceptable carrier. Pharmaceutically acceptable carriers are preferably liquid, particularly aqueous, carriers. For the purpose of preparing such vaccine formulations, the IFN and live virus may be mixed in sodium phosphate-buffered saline (pH 7.4) or conventional culture media. The vaccine formulation may be stored in a sterile glass container sealed with a rubber stopper through which liquids may be injected and formulation withdrawn by syringe. Those skilled in the art will appreciate that pharmaceutical formulations may be formulated containing IFN and two or more vaccine organisms. Such multiple vaccine formulations are advantageous because of practical considerations, e.g., time, cost, minimize handling of the subject.

Vaccine formulations of the present invention may optionally contain one or more adjuvants. Any suitable adjuvant can be used, including chemical and polypeptide immunostimulants that enhance the immune system's response to antigens. Preferably, adjuvants such as aluminum hydroxide, aluminum phosphate, plant and animal oils, and the like are administered with the vaccine in an amount sufficient to enhance the immune response of the subject to the vaccine. The amount of adjuvant added to the vaccine will vary depending on the nature of the adjuvant, generally ranging from about 0.1 to about 100 times the weight of the composition containing the virus, preferably from about 1 to about 10 times the weight of the composition containing the virus.

The vaccine formulations of the present invention may optionally contain one or more stabilizers. Any suitable stabilizer can be used, including carbohydrates such as sorbitol, manitol, starch, sucrose, dextrin, or glucose; proteins such as albumin or casein; and buffers such as alkaline metal phosphate and the like.

E. Vaccine Administration to Maternal Antibody Positive Animals.

It is well-known in the veterinary, poultry and animal sciences that the presence of maternally-transmitted antibodies in the hatchling bird or young mammal adversely affects vaccine efficacy. Resistance to vaccines in young mammals and avians is a persistent problem to which considerable efforts have been directed by the animal and poultry industries. See, e.g., Kit et al., (1993) *Immunology and Cell Biology* 71:421 (pigs); Xiang et al., (1992) *Virus Res.* 24:297 (mice); van Oirschot et al., (1991) *J. Vet. Med.* 38:391 (horses); Bjoerkholm et al., (1995) *Pediatric Infectious Disease J.* 14:846 (humans); Tsukamoto et al., (1995) *Avian Dis.* 39:218 (chickens). The problem is particularly acute with respect to live vaccines. Tsukamoto et al., (1995) *Avian Dis.* 39:218. Unfortunately, there has been little success in overcoming the problem of inactivation of vaccines by maternal antibodies. Rather, most vaccination programs in young animals are designed to circumvent maternal antibodies by delaying vaccination until after maternal antibody levels decline or disappear.

The present investigations have led to the discovery that the administration of IFN, in particular IFN-I, in conjunction with vaccines can overcome the neutralizing (i.e., inhibitory or inactivating) effects of maternal antibodies and, thus, lead to more effective vaccination programs for maternal antibody positive animals. Typically, the maternal antibodies neutralize, inhibit and/or inactivate the vaccine by recognizing (i.e., specifically binding to) the vaccine immunogen. By a "maternal antibody positive" animal it is meant an animal that has passive immunity by the transmission of maternal antibodies, i.e., from colostrum, milk or the egg yolk. Alternatively stated, the animals are seropositive for the vaccine organism as a result of maternally-transmitted antibodies. As a further alternative, a "maternal antibody positive" animal still has sufficient maternally-transmitted antibodies, such that their presence will substantially interfere with vaccine efficacy (e.g., 20%, 30%, 40%, 50%, 70%, or more), as this term is understood in the art (e.g., reduction in titers, reduction in ability to withstand a challenge, and the like).

This embodiment of the invention is preferably, and advantageously, employed with vaccines that would generally be unsafe (e.g., a vaccine associated with hatch depression). However, if lower "safe" doses of vaccine are administered in the absence of IFN, they may not be efficacious because of the interference by maternal antibodies. While not wishing to be held to any particular theory of the invention, it appears that administration of vaccine in combination with interferon according to the present invention, allows the administration of vaccine doses sufficient to overcome the interfering effects of maternal antibodies. In the absence of IFN, these doses would generally result in unacceptable levels of morbidity and mortality in the host birds. The IFN reduces the pathogenic effects of the virus, as described hereinabove, such that higher, more efficacious, doses of vaccine can be safely administered.

Live virus vaccines are preferred, with live pathogenic virus vaccines being most preferred. Vaccines and interferon for use according to this embodiment of the invention, methods of administration thereof, and pharmaceutical formulations are as described above.

Vaccines can be administered according to the present invention to birds in ovo and to hatchlings to administer high enough virus doses to overcome the interfering effects of maternal antibodies without compromising safety. Avian subjects are as described above. In bird embryos, maternal antibodies are deposited in the yolk and are taken up by the embryo as the yolk is resorbed. Typically, maternal antibodies can be detected in the embryo by embryonic day 15. Accordingly, the present invention is useful in increasing the efficacy of vaccines administered after embryonic day 15, more preferably after embryonic day 17, to birds in ovo.

Unlike conventional vaccination methods, the inventive methods disclosed herein may be carried out to vaccinate a young bird soon after hatch. In young chickens, maternal antibodies generally disappear by three weeks after hatch.

Accordingly, in young birds, vaccine and interferon are administered within about four weeks post-hatch, preferably within about three weeks post-hatch, more preferably within about two weeks post-hatch, still more preferably, within about one week post-hatch, and most preferably within about the first three days post-hatch. Typically, vaccination will be carried out at the time that the birds are transferred from the hatcher (usually one or two days post-hatch).

In other preferred embodiments, the invention may be practiced to more effectively vaccinate young mammals, even in the presence of maternal antibodies. Maternal antibodies are passed to the young mammal through the colostrum and, to a lesser extent milk, and disappear in the first few months after birth. Vaccination of young pigs by conventional methods, for example, is generally carried out at about three weeks of age, about the time that maternal antibodies have disappeared and the young animal's own active immune responses are increasing.

The terms "mammal" and "mammalian subject", as used herein, include the male and females of any mammalian species. Preferred are humans, domestic livestock (e.g., horses, cattle, sheep, pigs and goats, and the like), and companion animals (e.g., cats, dogs, guinea pigs, gerbils, hamsters, and the like). Most preferred are domestic livestock species.

Any appropriate method of administering vaccines and interferon to young mammals may be employed. Exemplary means are oral administration (e.g, by "drenching", or by administration in the feed or drinking water), intramuscular injection, subcutaneous injection, intravenous injection, intra-abdominal injection, eye drop, or nasal spray. The young mammal may be a neonate (i.e., about the first one to three days after birth). Alternatively, the animal may be less than about one week in age, less than about two weeks in age, less than about three weeks in age, less than about four weeks in age, less than about six weeks in age, less than about eight weeks in age, or less than about twelve weeks in age. Those skilled in the art will appreciate that the precise timing and method of administration depends on the vaccine, the age, condition and species of the subject, and practical and logistical considerations relating to the conditions in which the animal is being raised (e.g., a pet dog versus a large commercial swine operation).

The following Examples are provided to illustrate the present invention, and should not be construed as limiting thereof. The abbreviations used in the Examples are defined as follows: "g" means gram, "mg" means milligram, "µg" means microgram, "L" means liter, "mL" means milliliter, "mol" means mole, "M" means molar, "mM" means millimolar, µM means micromolar, "m" means meter, "mm," means millimeter, "nm" means nanometer, "Da" means daltons, "kDa" means kilodaltons, "w/v" means weight per volume, "v/v" means volume per volume, "C" means Celsius, "SPF" means specific pathogen free, "HI" means hemagglutination inhibition, NDV means Newcastle disease virus, and "IFN" means interferon.

EXAMPLE 1

Materials and Methods

Recombinant chicken interferon-I (IFN-I) was expressed in the yeast *Pichia pastoris*. Briefly, four primers (designated IFN-I through IFN-4) were designed based on the published sequence for type I IFN by Sekellick et al., (1994) *J. Interferon Res.* 14:71. Primer IFN-3 was designed as a reverse transcription primer. It is antisense to the mRNA and located 3' to the termination of the coding region. The IFN-1 and IFN-2 primers were designed to amplify the portion of the cDNA encoding the mature protein. Both primers contain EcoRi sites engineered onto the 5' ends to facilitate subcloning of the IFN cDNA into the *Pichia pastoris* pPIC9 expression vector in-frame with the secretion signals encoded by the plasmids. Primer IFN-4 was derived from an internal cIFN mRNA sequence to facilitate sequence analysis.

Total RNA prepared from chicken splenocyte cultures was reverse transcribed with the RNA-PCR kit (Perkin-Elmer) priming with either random hexamers or primer IFN-3. PCR amplification was performed with primers IFN-1 and IFN-2 using the RNA-PCR reagents plus 10% glycerol. Taq polymerase was added separately after pre-heating the other reagents to 95° C. for 2 minutes. Amplification proceeded for 5 cycles of 95° C., 1 minute; 50° C., 2 minutes; 72° C., 1 minute; followed by 25 cycles of 95° C. 1 minute; 60° C., 2 minutes; 72° C., 3 minutes. Analysis of the PCR products showed a single band of ~500 bp. The IFN PCR product was subcloned into the pCRII® plasmid vector (Invitrogen, Carlesbad, Calif.) according to the manufacturer's protocol. Two positive clones, selected by restriction enzyme analysis were confirmed by DNA sequencing. These clones were sequenced in their entirety and were found to have no base pair changes compared with the published sequence for IFN-I.

IFN-I excised from the pCRII® vector with EcoRI was subcloned into the EcoRl site of the pPIC9 vector (Invitrogen, San Diego, Calif.) in frame with the α-F mating factor secretion signal provided in the vector. pPIC9-IFN-I, linearized by digestion with Bg/II, was isolated from soft agarose and transformed into spheroplasts of the *Pichia pastoris* strain, GS115(HIS−). The yeast were plated onto minimal media for selection of His+ transformants. Transformants were then plated on selective media that allows identification of recombinants that have the pPIC9-IFN-I cDNA integrated into the yeast genome at the AOXI locus. Selected His+ Mut$^S$ clones were grown using standard growth and induction methods. Methanol-induced cell free supernatants of sixteen cIFN-I transformed *Pichia pastoris* clones were media exchanged on 10 kDa centricon concentrators (Amicon, Danvers, Mass.) and assayed in a chick embryo fibroblast viral protection bioassay. Ten clones exhibited good activity compared with controls. Bioactive IFN-I preparations were combined, concentrated and evaluated by coomassie blue and silver staining of SDS-PAGE gels. The IFN-I banding pattern was complex with a number of bands in the 21–45 kDa range, including a predominant band at approximately 31 kDa. One bioactive clone was selected for scale-up production and evaluation of in vivo activity.

Yeast expressing the chicken IFN-I are grown using standard growth and induction techniques. Yeast cells are removed by centrifugation, and the supernate is clarified by microfiltration. The IFN-I is further processed by concentration and buffer exchange using a 10 kilodalton ultrafiltration membrane. In an optional step, the processed recombinant IFN-I may be further purified by reverse phase HPLC using gradient elution, and the organic mobile phase components are then removed by vacuum evaporation. The final IFN-I preparation is sterile-filtered and stored at −4° C. to −70° C., typically −20° C. to −10° C, until use. Each IFN-I batch is analyzed for protein concentration and sterility.

These studies used protein level for determining IFN-I dose. Batch-to-batch specific activity was calculated on the basis of the in vitro chick embryo fibroblast viral protection bioassay. J. E. Cooligan et al., *Current Protocols in Immunology*, 6.9.1–6.9.3 (1995). The specific activity ranged from $1 \times 10^5$ to $1 \times 10^8$ units/mg protein. Protein determinations were made using the BioRad kit (Hercules, Calif.). Relative protection from IFN-I treatment was consistent among batches.

The Newcastle Disease Virus (NDV) vaccine was the B1 Type, LaSota Strain Live Virus, CLONEVAC-30 NDV vaccine from Intervet, Inc. (Millsboro, Del.). Specific Pathogen Free (SPF) leghorn eggs were obtained from Hy-Vac (Adel, Iowa). Broiler eggs (Cobb×Cobb) were obtained from Central Farms (Fayetteville, N.C.) or from Green Forest Hatchery (Green Forest, Ark.).

Egg injection was performed on embryonic day 18 (E18) embryos by injection into the anmion of test article in 100 μl. Confirmation of injection site was performed by injection of latex dye and breaking out the embryo to visually observe site of injection. Unless noted otherwise, hatch was routinely monitored at day E22, and unhatched eggs broken out to determine whether embryonic death was related to treatment or not (e.g., middle death, malformed, etc.). Cumulative survivability was determined at indicated time points by taking the number of surviving hatched chicks at a given time-point divided by the number of eggs incubated minus death unrelated to treatments.

Statistical methods, where applicable, are indicated in the descriptions of individual experiments.

EXAMPLE 2

Hatchability and Survivability of Chicks Vaccinated in ovo with Newcastle Disease Vaccine This study was undertaken to investigate the relationship between in ovo NDV vaccine dose and hatchability. Treatment groups of either PBS or a $10^4$, $10^2$, 1, or $10^{-2}$ $EID_{50}$ dose of NDV vaccine were administered to day E18 embryos via amnion injection into 40 double-candled, Hyvac SPF eggs per treatment group.

Figure 2:
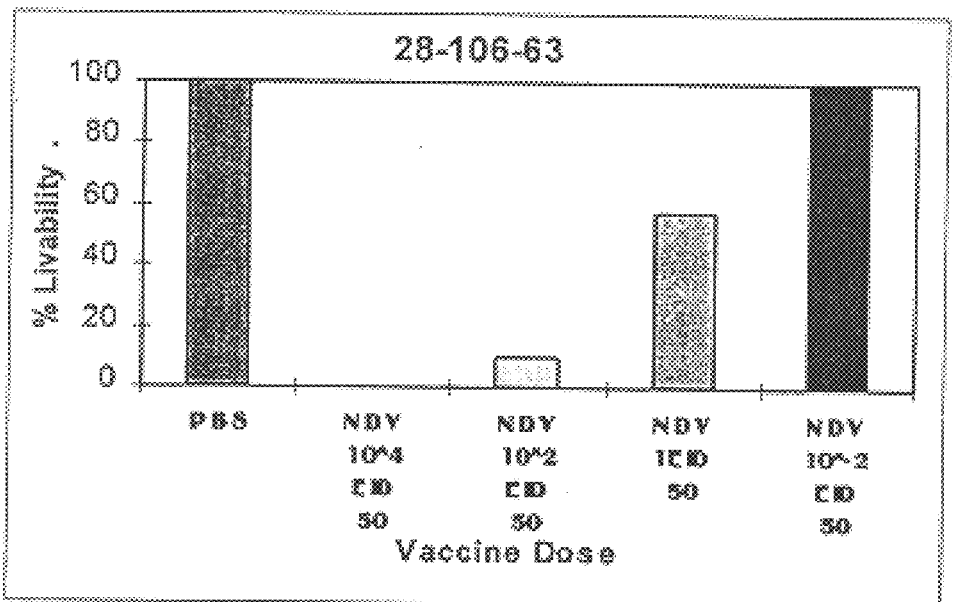
FIG. 2 is a graphical representation of the effects of in ovo NDV dose on 7-day post-hatch mortality of SPF chicken embryos. These data were collected as part of the same study presented in FIG. 1. Eggs were administered either PBS or a $10^4$, $10^2$, 1 or $10^{-2}$ $EID_{50}$ dose of NDV vaccine on embryonic day 18, and survivability was monitored for 7 days post-hatch. There were 40 eggs per treatment group.
Figure 3:
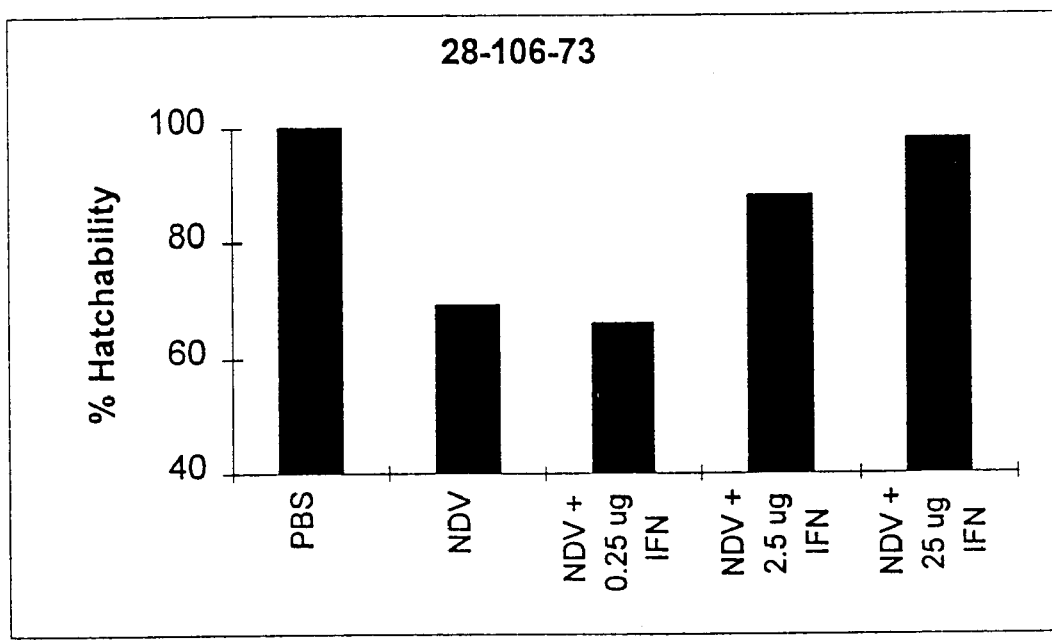
FIG. 3 is a graphical representation of the effects of IFN-I administration in conjunction with NDV vaccination in ovo on hatchability of SPF chicken eggs. On embryonic day 18, eggs were co-administered a 1 $EID_{50}$ dose of NDV vaccine together with PBS or 0.25, 2.5 or 25 µg IFN-I, and hatchability was monitored for each treatment group. There were 60 eggs per treatment. Controls received PBS alone.
Figure 4:
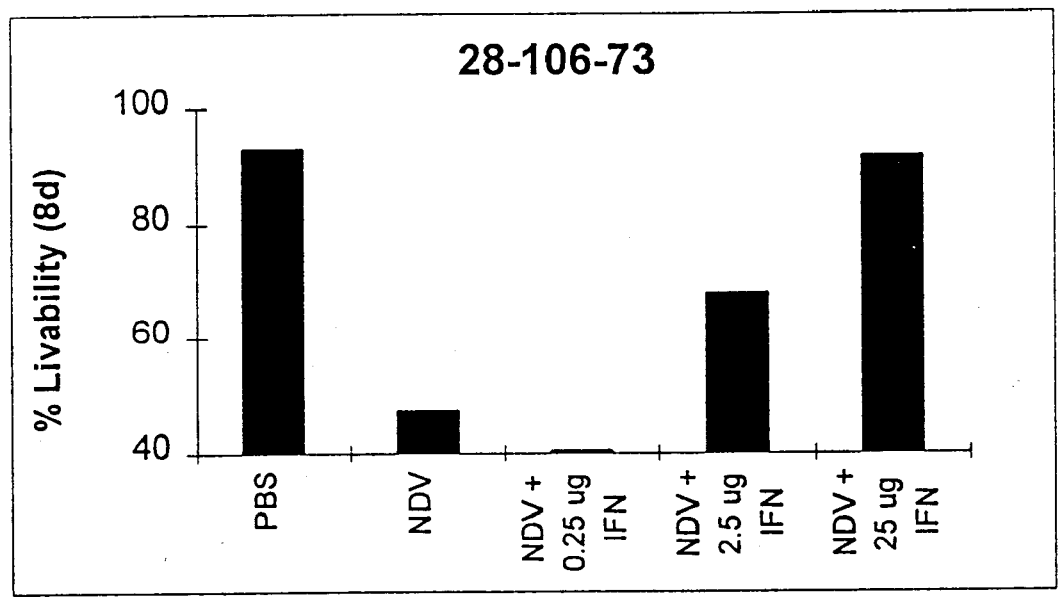
FIG. 4 is a graphical representation of the effects of IFN-I administration in conjunction with NDV vaccination in ovo on 8-day post-hatch survival of SPF chicks. These data were collected as part of the same study presented in FIG. 3. On embryonic day 18, eggs were co-administered a 1 $EID_{50}$ dose of NDV vaccine together with PBS or 0.25, 2.5 or 25 µg IFN-I, and survivability was monitored for 8 days after hatch. There were 60 eggs per treatment. Controls received PBS alone. Data are inclusive of embryonic mortality.
Figure 5:
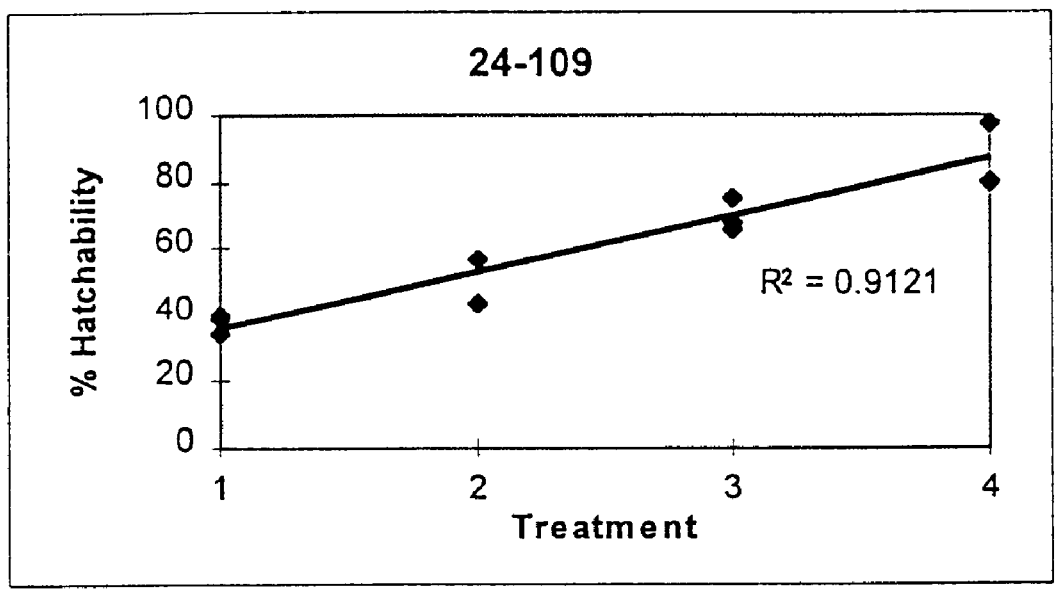
FIG. 5 is a graphical representation of the effects of IFN-I administration in conjunction with NDV vaccination in ovo on hatchability of SPF chicken eggs. Data were collected from three separate trials with 25 to 40 eggs per treatment group, depending on the trial. All treatments received NDV vaccine at a 10 $EID_{50}$ dose and either no IFN-I (treatment 1) or 0.2, 2.0 or 20 µg IFN-I (treatments 2–4, respectively) in ovo. Hatchability was monitored for each treatment group. The results for each treatment were averaged across the three trials.
Figure 6:
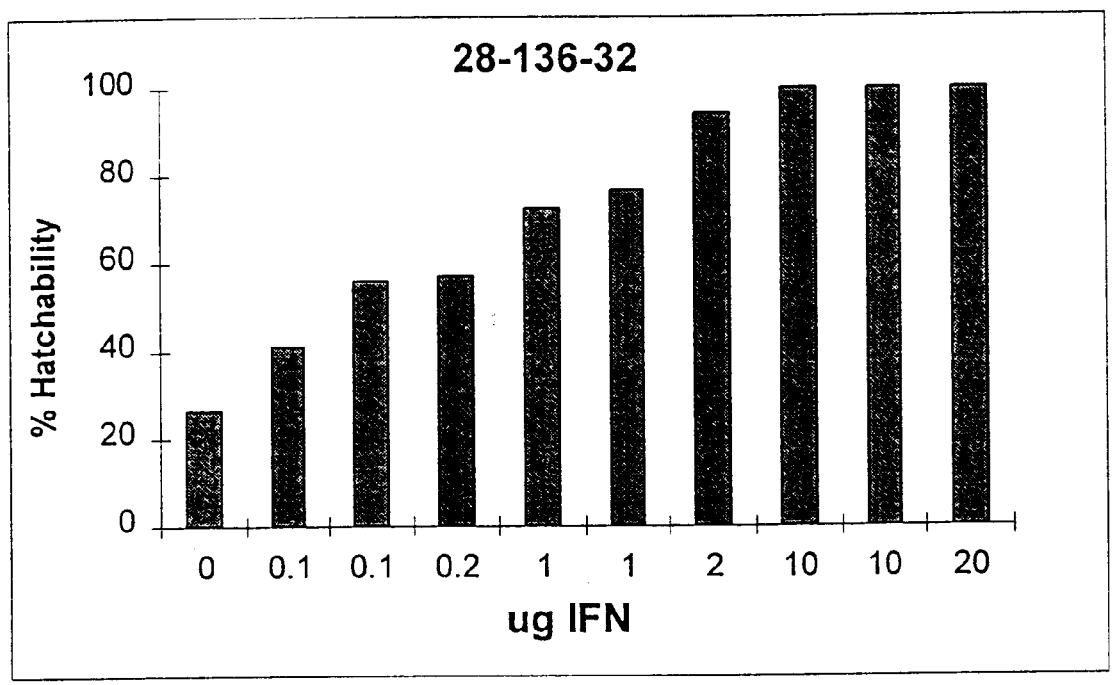
FIG. 6 is a graphical representation of the effects of IFN-I administration in conjunction with NDV vaccination in ovo on hatchability of SPF chicken eggs. Day 18 embryonic eggs were administered 10 $EID_{50}$ NDV vaccine with PBS or 0.1, 0.2, 1.0, 2.0, 10 or 20 µg IFN-I per egg. There were 32 eggs per treatment group.

Hatchability and seven-day mortality results are shown in FIG. 1 and FIG. 2, respectively. The seven-day mortality data in FIG. 2 include embryo mortalities. Survivability results show an approximately 10% decrease in hatchability for the 1 $EID_{50}$ treatment group with an overall 40% mortality of birds post-hatch (inclusive of embryo mortality) for this same treatment group.

EXAMPLE 3

Assessing Safety of in ovo IFN-I Administration

An experiment was performed to determine whether IFN-I administration to day E18 chick embryos is safe. Interferon-I at a dose of 0.00025, 0.025 or 2.5 μg was administered to 10 eggs per treatment group and hatchability determined. As shown below on Table 1, none of the IFN treatments resulted in hatchability less than that observed in the PBS injected controls, indicating no overt safety problems with IFN-I administration at these doses.

TABLE 1

Hatchability of Chicks Administered IFN-I on Embryonic Day 18

| Treatment | Hatchability |
|---|---|
| PBS | 80% |
| 0.00025 μg IFN-I | 100% |

TABLE 1-continued

Hatchability of Chicks Administered IFN-I on Embryonic Day 18

| Treatment | Hatchability |
|---|---|
| 0.025 μg IFN-I | 80% |
| 2.5 μg IFN-I | 100% |

EXAMPLE 4

Interferon -I Protects Chicks from the Lethal Effects of in ovo Vaccination Against NDV This experiment was performed to determine whether IFN-I administration protects chicks against the lethal effects of NDV vaccination in ovo. Day E18 eggs were administered 1 $EID_{50}$ dose of NDV. Birds were co-administered PBS (vaccine control) or 0.25, 2.5 or 25 μg IFN-I. A control group received PBS only, in ovo. Hatchability and survivability results are shown in FIG. 3 and FIG. 4, respectively. NDV vaccination alone resulted in approximately 30% mortality in ovo and 50% mortality post-hatch (8 day mortality, including lethal effects on embryo), but these lethal effects were overcome by simultaneous administration of 25 μg IFN-I (FIG. 4). The protective effects of IFN-I were dose-dependent, with more protection being observed with administration of 25 μg versus 0.25 μg IFN-I.

EXAMPLE 5

Dose-Response with in ovo IFN-I: Study 1

The objective of this study was to ascertain IFN-I doses for in ovo administration in conjunction with NDV vaccination. Day E18 eggs (25–40 eggs per treatment) were injected with PBS, 10 $EID_{50}$ NDV, or 10 $EID_{50}$ NDV+0.2, 2.0 or 20 μg IFN-I. Hatchability was assessed for each treatment group. This experimental protocol was carried out in 3 separate trials. The results are shown in FIG. 5. Two outliers (treatments 2 and 4) were removed from the third trial due to technical error. The precision within trials is very good (CV of 2.1% and 7.7% for the PBS and vaccine control groups, respectively).

The repeatability of the ameliorative effects of IFN-I on mortality induced by NDV vaccine administration was excellent in the first two trials, but not in the third trial. Further analysis of this data, having first excluded the outliers, demonstrates a dose-dependent effect of IFN-I in ameliorating mortality from NDV vaccination in ovo. Some degree of ameliorative effects were observed at all doses of IFN-I, with 20 μg IFN-I co-administration with NDV vaccine giving the same hatchability as PBS controls.

EXAMPLE 6

Dose-Response with in ovo IFN-I: Study 2

A second IFN-I dose-response study was carried out on a single set of birds, essentially as described in Example 5. Day E18 eggs were vaccinated with 10 $EID_{50}$ dose of NDV vaccine alone, or in combination with 0.1, 0.2, 1.0, 2.0, 10, or 20 μg IFN-I. A non-vaccinated control (PBS), which did not receive IFN-I, was also included in the experimental design and had 100% hatchability (data not shown). There were 36 eggs per treatment group. As seen in FIG. 6, IFN-I had protective effects on hatchability at all doses tested. A dose-dependent protection was observed, with complete protection at 10 μg/egg and higher.

EXAMPLE 7

Dose-Response with in ovo IFN-I: Study 3

Figure 7:
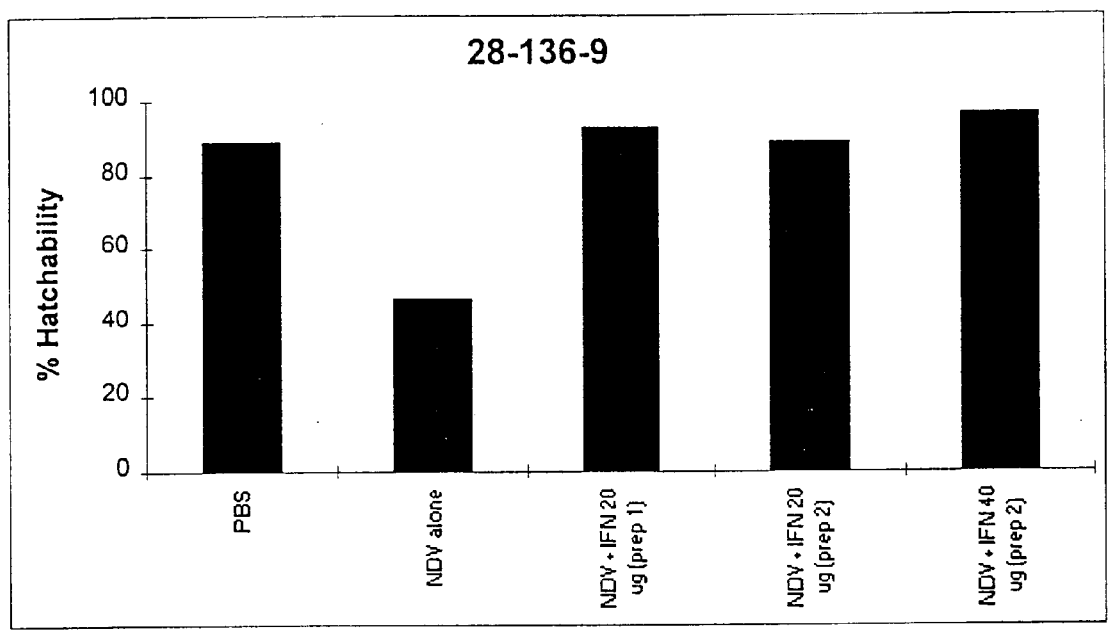
FIG. 7 is a graphical representation of the effects of IFN-I administration in conjunction with NDV vaccination in ovo on hatchability of SPF chicken embryos. Day 18 embryonic eggs were administered 10 $EID_{50}$ NDV vaccine together with 0, 20 or 40 µg IFN-I per egg. Two different IFN-I preparations were assessed in this study. One treatment group received PBS alone (positive control) There were 27 eggs per treatment group.

This study evaluated higher doses of IFN-I as a follow-up to the studies presented in Example 5 and Example 6. IFN-I at a concentration of 0, 20 or 40 μg/egg was co-injected with 10 $EID_{50}$ NDV into day E18 eggs. Two preparations of IFN-I were assessed. Each treatment group included 27 eggs. Hatchability was determined for each treatment (FIG. 7). Protection was seen at 20 μg (both preparations) and 40 μg IFN-I. In a separate study, yeast expressed albumin (YEA) was injected as a negative control for IFN-I administration to ensure that protection is not a result of by-products of the IFN-I expression in the yeast *Pichia pastoris*. No amelioration of mortality associated with NDV vaccine administration was observed in the YEA control group (data not shown).

EXAMPLE 8

Administration of IFN-I with Increasing NDV Vaccine Dose-Study 1

Figure 8:
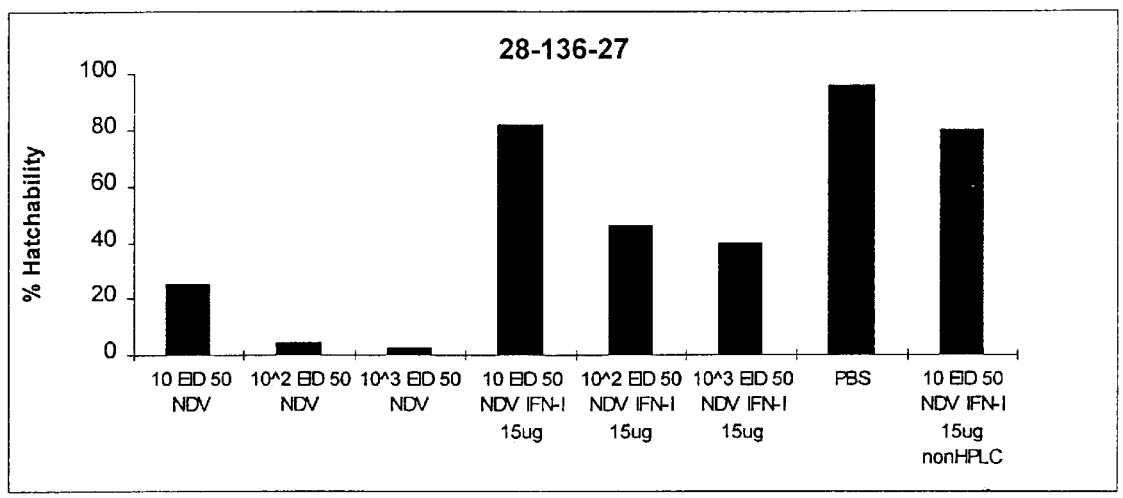
FIG. 8 is a graphical representation of the effects of IFN-I administration in conjunction with increasing doses of NDV vaccine in ovo on hatchability of SPF chicken embryos. Embryonic day 18 eggs were administered 15 µg IFN-I together with 10, $10^2$, or $10^3$ $EID_{50}$ NDV, and hatchability was monitored for each treatment group. The positive control group received PBS alone. There were 47 eggs per treatment group. In addition, a comparison was performed between administration of HPLC purified IFN-I versus non-HPLC purified IFN-I in the presence of 10 $EID_{50}$ NDV.

The purpose of this study was to determine the extent of the protection provided by IFN-I to SPF embryos administered larger doses of NDV vaccine. One dose (15 μg) of IFN-I was co-administered with one of three doses of virus (10, $10^2$, and $10^3$ $EID_{50}$ dose) to day E18 eggs (47 eggs per treatment group). Hatchability was determined for each treatment group. As seen in FIG. 8, 15 μg of IFN-I was found to be protective for all virus doses. However, the degree of protection was not equivalent to the hatchability noted in animals not receiving NDV vaccine (PBS group). In addition to the main focus of the experiment, 10 $EID_{50}$ dose of NDV administered with non-HPLC purified IFN-I was compared with the same NDV dose administered with HPLC purified IFN-I for efficacy in preventing NDV vaccine-induced lethality. In this study, on a protein basis, the two preparations appeared equivalent in protecting embryos from NDV vaccine challenge.

EXAMPLE 9

Administration of IFN-I with Increasing NDV Vaccine Dose—Study 2

Figure 9:
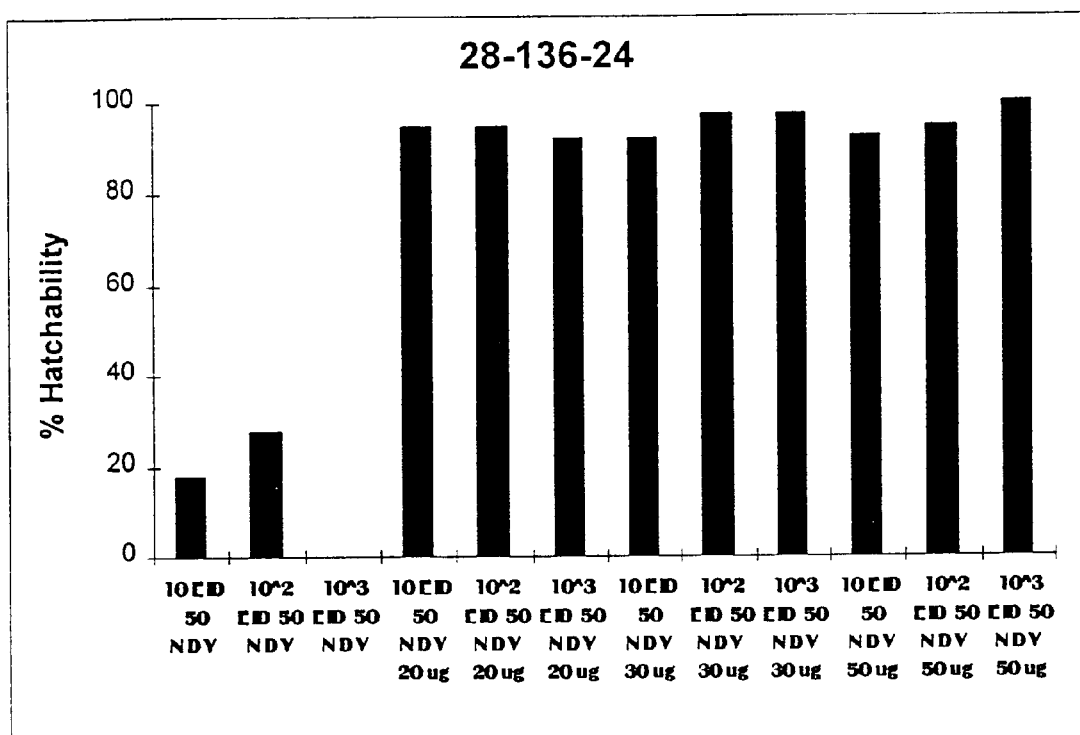
FIG. 9 is a graphical representation of the effects of IFN-I administration with increasing doses of NDV vaccine in ovo on hatchability of SPF chicken embryos. Embryonic day 18 eggs were co-administered 20, 30 or 50 µg IFN-I per egg in conjunction with 10, $10^2$ or $10^3$ $EID_{50}$ NDV, and hatchability was monitored for each treatment group. There were 40 eggs per treatment group.

This study evaluated varying doses of both NDV vaccine and IFN-I on hatchability of SPF embryos. Three doses of IFN-I (20, 30 and 50 μg/egg) were co-administered with one of three doses of virus (10, $10^2$, and $10^3$ $EID_{50}$ dose) to day E18 eggs (40 eggs/treatment). Hatchability was determined for all treatment groups (FIG. 9). As seen in FIG. 9, IFN-I was found to be protective at 20 μg and above at all doses of NDV vaccine. Significantly, protection was extended to embryos co-administered a $10^3$ $EID_{50}$ dose of the vaccine, a dose that was 100% lethal in positive controls.

EXAMPLE 10

Survival of IFN-I Treated Chicks Vaccinated Against NDV in ovo

Figure 10:
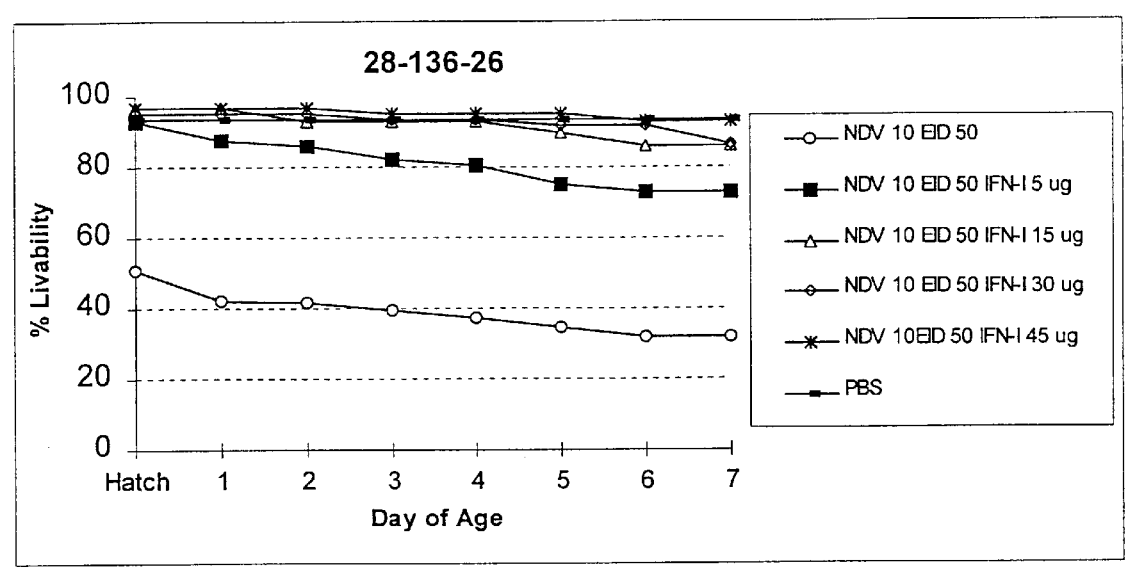

In this study, the protective effects of IFN-I were evaluated by survival over 7 days post-hatch. Four doses of IFN-I (5, 15, 30 and 45 μg/egg) were co-administered with a 10 $EID_{50}$ dose of NDV vaccine on day E18 (60 eggs/treatment group). Assessment of hatchability indicated that as low as 5 μg/egg of IFN-I is protective when co-administered with 10 $EID_{50}$ dose NDV vaccine to day E18 embryos (FIG. 10). As shown in FIG. 10, all doses of IFN-I showed significant protection over the entire 7-day period post-hatch. Cumulative survivability, however, showed that complete IFN-I protective effects (equivalent % livability to non-"challenged" control group) lasting through the 7 day grow-out period were only seen in the 45 μg/embryo treatment group.

EXAMPLE 11

Cumulative Survivability Study with Increasing Vaccine Dose

Figure 11:
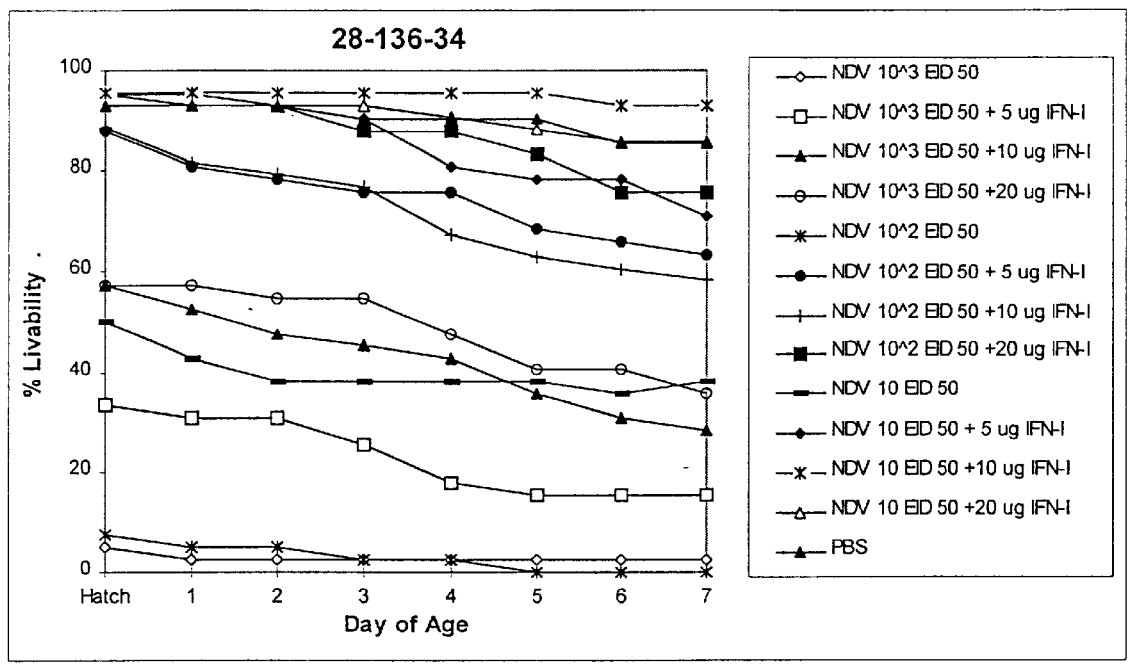
FIG. 11 is a graphical representation of the effects of IFN-I co-administration with NDV vaccination in ovo on 7-day post-hatch survivability of SPF chicken embryos. Embryonic day 18 eggs were co-administered 0, 5, or 20 µg IFN-I per egg together with 10, $10^2$ or $10^3$ $EID_{50}$ NDV vaccine, and survivability was monitored for 7 days following hatch. One treatment group only received PBS (positive control). There were 43 eggs per treatment group.
Figure 12:
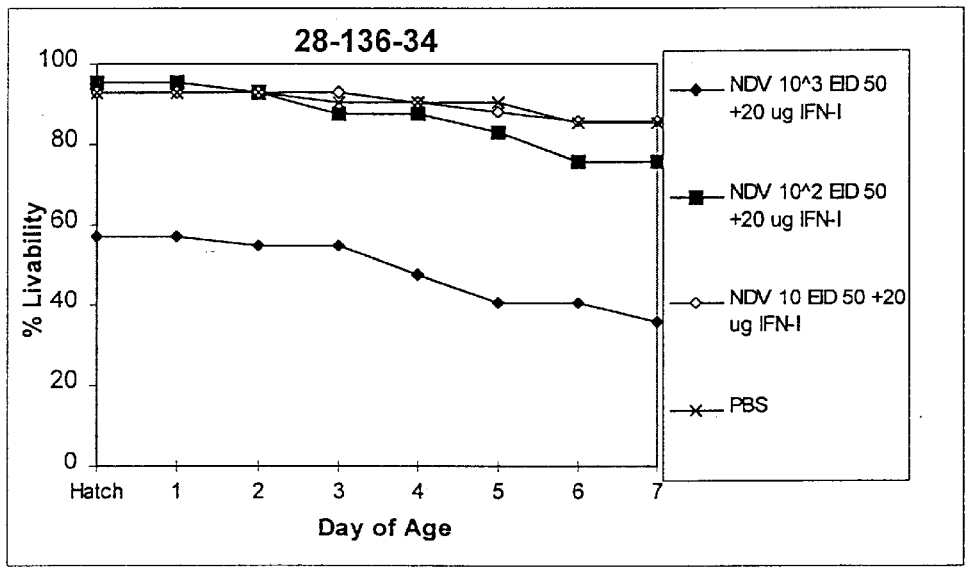
FIG. 12 is a graphical representation of the data from FIG. 11 showing only the treatment groups receiving 20 µg IFN-I per egg together with 10, $10^2$ or $10^3$ $EID_{50}$ NDV vaccine, as well as the positive control (PBS) group.
Figure 13:
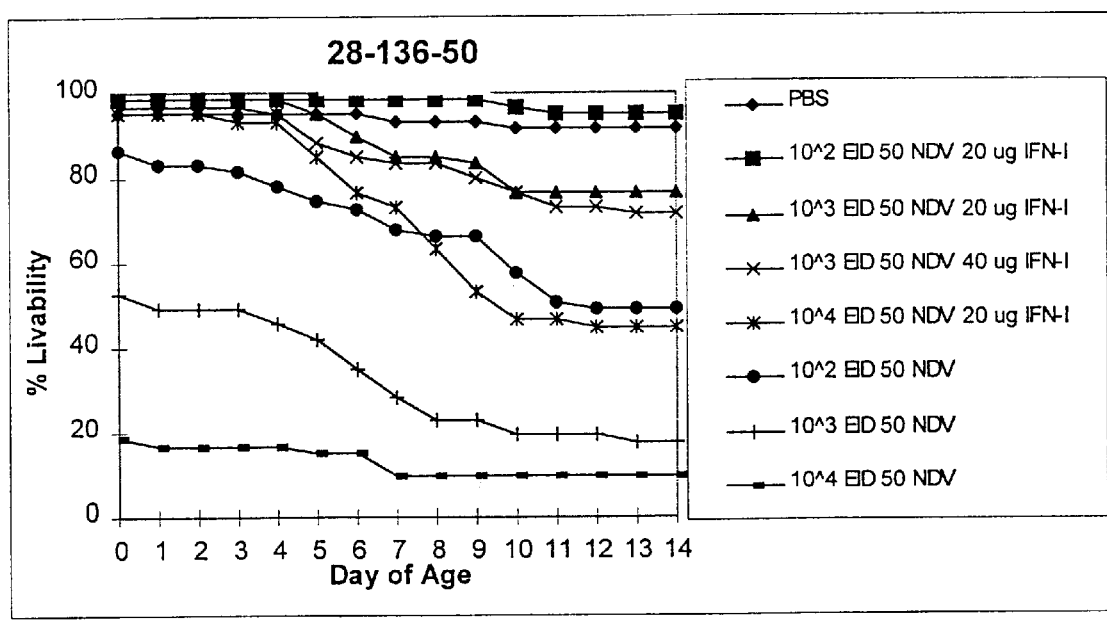
FIG. 13 is a graphical representation of the effects of co-administration of IFN-I and NDV vaccine in ovo on hatchability and 14-day survivability of commercial broilers. The positive control only received PBS. Embryonic day 18 eggs were co-administered with 0, 20 or 40 µg IFN-I per egg in conjunction with 0, $10^2$, $10^3$ or $10^4$ $EID_{50}$ NDV vaccine. Hatchability and 14-day post-hatch survivability were monitored for each treatment group. There were 60 eggs per treatment group.

Survivability data was collected for varying concentrations of IFN-I. This study was performed to examine the protective effects of IFN-I (5, 10 and 20 μg/egg) on survivability when co-administered with three different doses of NDV vaccine (10, $10^2$, and $10^3$ $EID_{50}$ dose) on day E18. Each treatment group included 43 eggs. FIG. 11 illustrates data collected from all treatment groups within the study. Some degree of protection was seen across all vaccine and IFN-I doses. FIG. 12 focuses on data collected over each NDV concentration dosed with 20 μg/egg of IFN-I. Protection lasted throughout the grow-out period with 20 μg IFN-I in animals receiving the $10^2$ or 10 $EID_{50}$ doses. Animals receiving the $10^3$ $EID_{50}$ dose of virus initially showed a substantial increase in survival with 20 μg IFN-I administration (over $10^3$ $EID_{50}$ alone), but this protective effect diminished following day 3 post-hatch.

EXAMPLE 12

Safety and Efficacy of IFN-I-NDV in SPF Embryos

A study was performed to more fully investigate the extent and the duration of both protection and protective titers in SPF animals challenged with a virulent strain of NDV. Embryos (E18) received IFN-I/NDV vaccine (10 or $10^2$ $EID_{50}$ dose of vaccine ±20 or 40 μg IFN-I) or relevant positive and negative controls. Each treatment group was kept under isolation conditions. The experimental design is indicated in Table 2 below. Representative groups of animals from each treatment group (10 animals/treatment group) were monitored for HI titer development and weight gain. Hatchability, pre-challenge survival (%), and body weights were also determined (Table 3; % survival not inclusive of embryonic mortality). Group 2 birds served as a control; they did not receive the NDV vaccine in ovo, but did receive a NDV vaccine (B1,B1 strain) intraocular post hatch. Surviving animals were challenged with the Texas GB strain of NDV at 3 weeks of age ($10^2$ $EID_{50}$, intramuscularly). Post-challenge mortality was monitored for a period of 2 weeks. Survival data shown in Table 3 indicate complete protection of one group of animals receiving the IFN-NDV (treatment 5/5a; administered with $10^2$ $EID_{50}$ NDV+20 μg IFN-I).

The protection data had excellent agreement with hemagglutination inhibition titers from representative animals in each treatment groups (Table 3). From the data in Table 3, it appears that a $10^2$ $EID_{50}$ dose of NDV with 20 μg of IFN-I is safe and, most importantly, is efficacious. The IFN-I (40 μg) with $10^2$ $EID_{50}$ NDV was safe for the SPF animals, but the treatment was not efficacious (i.e., the animals were not protected from a NDV challenge). It is possible that, in this instance, the 40 μg IFN-I may be so efficient at blocking viral replication that the birds did not develop immunity. With lower virus (10 $EID_{50}$ NDV) and 20 μg IFN, the two replicates were each safe, but only one replicate proved efficacious (i.e., could protect the birds against a NDV challenge). It appears that, in some instances, one can administer too much IFN-I, so that vaccine efficacy is impaired. However, when administered at optimal amounts of virus and IFN combinations, the vaccine is both safe and efficacious, as in treatment group 5.

TABLE 2

| Experimental Treatment Groups and Hatchability | | |
|---|---|---|
| Group | N | Vaccination |
| 1,1a<br>PBS | 50 | E18 in ovo |
| 2,2a<br>PBS<br>NDV (B1, B1) vaccine<br>post hatch | 50 | PBS at E18<br>in ovo,<br>vaccine at<br>hatch |
| 3,3a<br>$10^2$EID$_{50}$ NDV | 250 | E18 in ovo |
| 4,4a<br>10EID$_{50}$NDV | 70 | E18 in ovo |
| 5,5a<br>$10^2$EID$_{50}$NDV +<br>20 $\mu$g IFN-I | 53 | E18 in ovo |
| 6,6a<br>$10^2$EID$_{50}$NDV +<br>40 $\mu$g IFN-I | 55 | E18 in ovo |
| 7,7a<br>10 NDV +<br>20 $\mu$g IFN-I | 52 | E18 in ovo |

EXAMPLE 13

Safety of IFN-I Administration in ovo to Maternal Antibody Positive Broilers This experiment was carried out to determine if effective NDV vaccine and IFN-I doses would be different for maternal antibody positive broilers as compared with SPF birds. For example, maternal antibody positive birds might require a higher virus dose and/or less IFN-I to elicit protection from the live virus vaccine. Day E18 Broiler eggs (Cobb×Cobb) were administered increasing doses of NDV vaccine ($10^2$, $10^3$, and $10^4$ EID$_{50}$ doses) in the presence and absence of 20 or 40 $\mu$g IFN-I. Note that $10^2$ EID$_{50}$ dose was optimal for experiments with SPF animals using this batch of vaccine. As shown in FIG. 13, survival was monitored at hatch (day 0) and during the 2-week grow-out period after hatch.

There was significant 2-week mortality when animals received any of the three doses of NDV without IFN-I. Two-week survival was equivalent among NDV treated birds co-administered with 20 $\mu$g IFN-I and $10^2$ EID$_{50}$ dose of vaccine and control birds receiving only PBS and vaccine in ovo. No difference was observed between 20 and 40 $\mu$g IFN-I co-administered with a $10^3$ dose of vaccine.

TABLE 3

| Treatment Group | Hatch % (Both Groups) | % Survival (day 21) | Body Weight (day 0) | Body Weight (day 21) | Body Weight (day 35) | Log 2 HI titers (Day 21) | Log 2 HI titers (Day 35) | % Protection |
|---|---|---|---|---|---|---|---|---|
| 1 - PBS | 98 | 100 | 38.1 | 184.4 | NS | 0.8 | NS | 0 |
| 1a - PBS | | 100 | 39.2 | 200.4 | NS | 0.8 | NS | 0 |
| 2 - PBS + post hatch NDV* | 74 | 100 | 38.5 | 182.5 | 352.9 | 7.1 | 8.8 | 100 |
| 2a - PBS + post hatch NDV* | | 100 | 37.7 | 170.5 | 329.6 | 7.3 | 6.1 | 100 |
| 3 - $10^2$ EID$_{50}$ NDV | 55 | 26 | 38.1 | 145.7 | 310.3 | 8.1 | 7.1 | 89 |
| 3a - $10^2$ EID$_{50}$ NDV | | 37 | 37.0 | 167.0 | 345.2 | 7.8 | 7.4 | 100 |
| 4 - 10 EID$_{50}$ NDV | 94 | 76 | 38.6 | 178.4 | 347.1 | 7.6 | 6.4 | 100 |
| 4a - 10 EID$_{50}$ NDV | | 72 | 38.8 | 170.4 | 326.1 | 8.0 | 7.1 | 100 |
| 5 - $10^2$ EID$_{50}$ NDV + 20 $\mu$g IFN | 96 | 88 | 37.5 | 186.3 | 354.6 | 7.3 | 7.4 | 100 |
| 5a - $10^2$ EID$_{50}$ NDV + 20 $\mu$g IFN | | 96 | 37.7 | 178.4 | 361.3 | 7.7 | 8.5 | 100 |
| 6 - $10^2$ EID$_{50}$ NDV + 40 $\mu$g IFN | 86 | 96 | 38.6 | 191.0 | NS | 1.0 | NS | 0 |
| 6a - $10^2$ EID$_{50}$ NDV + 40 $\mu$g IFN | | 100 | 38.1 | 182.4 | 213.6 | 1.0 | 12.0 | 4 |
| 7 - 10 EID$_{50}$ NDV + 20 $\mu$g IFN | 89 | 96 | 37.6 | 192.5 | NS | 1.1 | NS | 0 |
| 7a 10 EID$_{50}$ NDV + 20 $\mu$g IFN | | 100 | 38.1 | 202.8 | 387.3 | 6.1 | 8.6 | 83 |

*post hatch control was B1,B1 vaccine control.

These results indicate that $10^2$ $EID_{50}$ dose of NDV vaccine is effective for infecting maternal antibody positive broilers. Animals receiving higher doses of NDV with IFN-I were protected at hatch, but the protection did not last throughout the grow-out period. There appeared to be no benefit in giving a greater IFN-I dose for maternal antibody positive as compared with SPF birds, i.e., 40 μg of IFN-I afforded no more protection than did 20 μg of IFN-I.

EXAMPLE 14

Efficacy of in ovo Administration of IFN-NDV Vaccination in Maternal Antibody Positive Chickens In order to determine whether IFN-NDV would demonstrate efficacy in maternal antibody positive broilers when challenged with virulent NDV at 4 weeks post hatch, this study inoculated embryonic day 18 broiler embryos (Cobb× Cobb) with $10^2$ to $10^3$ $EID_{50}$ NDV in combination with 10–20 μg IFN-I per egg. Controls received only PBS in ovo or $10^3$ EID50 NDV without IFN-I. There were 60 to 200 eggs per treatment group. Each treatment group was kept in isolation from time of injection through growout. Hatchability, pre-challenge % survival, and body weights are shown (Table 4; % survival not inclusive of embryonic mortality).

As shown in Table 4, all animals tested had maternal antibodies at hatch, assessed by HI titers. By 4 weeks post-hatch, maternal antibodies had waned to non-protective levels in control animals, and protective HI titers had been established in all treatment groups receiving NDV vaccine in ovo. Although protective titers were established in the NDV treatment group not receiving IFN-I, this vaccine dose was clearly not safe without co-administration of IFN, as shown by the decreased hatchability of only 87%, a significant decrease in hatchability compared with the PBS controls ($p \geq 0.05$). When vaccine was administered in the presence of IFN-I, hatchability was similar to PBS treated controls.

At 4-weeks post hatch, 20 surviving birds from each treatment were challenged with a $10^2$ $EID_{50}$ NDV (Texas GB) challenge, and two-week survivability was monitored. The survivability data are presented as "% Protection" in Table 4 below. All treatment groups receiving IFN-NDV combinations in ovo were protected from virulent challenge.

The above Examples demonstrate IFN-NDV co-administration in ovo to be safe and efficacious for inducing protective immunity in SPF and maternal antibody positive chickens.

TABLE 4

| Treatment Group | Hatch % (Both Groups) | % Survival (day 28) | Body Weight (day 0) | Body Weight (day 28) | Body Weight (day 42) | Log 2 HI titers (Day 0) | Log 2 HI titers (Day 28) | Log 2 HI titers (Day 42) | % Protection |
|---|---|---|---|---|---|---|---|---|---|
| 1 - PBS | 97 | 100 | 44.0 | 1069.1 | 1759.7 | 3.5 | 0.9 | 9.0 | 5 |
| 1a - PBS | | 100 | 43.7 | 1076.4 | ns | | 0.7 | ns | 0 |
| 2 - $10^2$ $EID_{50}$ NDV + 20 μg IFN-I | 97 | 100 | 43.8 | 1145.0 | 2275.1 | 3.5 | 6.9 | 7.8 | 100 |
| 2a - $10^2$ $EID_{50}$ NDV + 20 μg IFN-I | | 92 | 44.2 | 1070.8 | 2123.1 | | 6.6 | 7.1 | 100 |
| 3 - $10^2$ $EID_{50}$ NDV + 10 μg IFN-I | 98 | 100 | 44.5 | 1110.5 | 2213.1 | 3.5 | 6.4 | 7.5 | 100 |
| 3a - $10^2$ $EID_{50}$ NDV + 10 μg IFN-I | | 100 | 44.0 | 1181.6 | 2340.5 | | 6.2 | 6.8 | 100 |
| 4 - $10^{2.5}$ $EID_{50}$ NDV + 20 μg IFN-I | 95 | 96 | 45.1 | 1132.5 | 2226.5 | 3.4 | 6.2 | 8.0 | 100 |
| 4a - $10^{2.5}$ $EID_{50}$ NDV + 20 μg IFN-I | | 96 | 45.2 | 1147.7 | 2164.1 | | 6.3 | 5.5 | 100 |
| 5 - $10^{2.74}$ $ID_{50}$ NDV + 20 μg IFN-I | 98 | 100 | 42.0 | 1118.2 | 2168.1 | 3.2 | 6.2 | 7.3 | 100 |
| 5a - $10^{2.74}$ $EID_{50}$ NDV + 20 μg IFN-I | | 100 | 43.0 | 1102.0 | 2045.6 | | 6.2 | 6.3 | 100 |
| 6 - $10^3$ EID 50 NDV + 20 μg IFN-I | 97 | 75 | 44.1 | 955.5 | 1975.0 | 3.6 | 6.6 | 6.9 | 100 |
| 6a - $10^3$ $EID_{50}$ NDV + 20 μg IFN-I | | 92 | 44.6 | 1042.1 | 2033.5 | | 7.5 | 5.9 | 100 |
| 7 - $10^2$ $EID_{50}$ NDV B1 LaSota | 87 | 79 | 43.2 | 892.3 | 1963.0 | 3.1 | 7.3 | 6.9 | 100 |
| 7a - $10^2$ $EID_{50}$ NDV B1 LaSota | | 86 | 43.8 | 929.0 | 1955.8 | | 6.6 | 7.0 | 100 |

EXAMPLE 15

Figure 14:
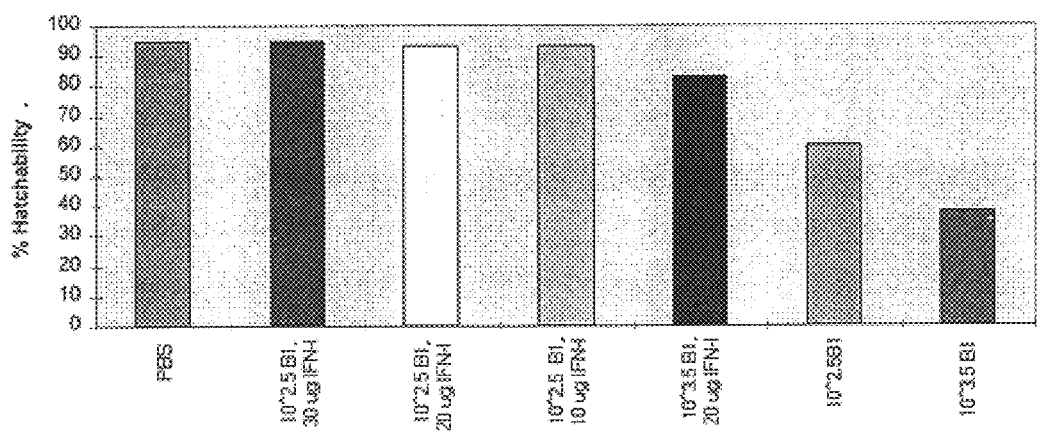
FIG. 14 is a graphical representation of the effects of co-administration of IFN-I and NDV vaccine in ovo on hatchability of commercial broilers. The positive control only received PBS. Embryonic day 18 eggs were co-administered with 0, 10, 20 or 30 µg IFN-I per egg in conjunction with 0, $10^{2.5}$ or $10^{3.5}$ $EID_{50}$ NDV vaccine. Hatchability was monitored for each treatment group.

Hatchability and Post-Challenge Survival of Maternal Antibody Positive Commercial Broilers Vaccinated in ovo with IFN-NDV Birds and vaccination were as described in Example 13 and Example 14. IFN-I (0, 10, 20 or 30 μg per egg) was co-administered with 0, $10^{2.5}$ $EID_{50}$ or $10^{3.5}$ $EID_{50}$ live NDV vaccine (Table 5). Hatchability of treated embryos was monitored (FIG. 14). Birds had a mean HI titer at hatch of 5.2 (Log 2) indicating a protective level of maternal antibody. Treatment groups were kept in isolation rooms until the time of challenge. Texas GB challenge occurred at day 28. Percent protection was determined by monitoring mortality for 14 days post challenge.

The hatch data in FIG. 14 indicate that NDV-IFN-I ($10^{2.5}$ $EID_{50}$+20 μg of IFN) is safe compared with in ovo NDV vaccine alone. The higher NDV vaccine dose ($10^{3.5}$ $EID_{50}$) in combination with 20 μg IFN was also protective compared with in ovo NDV vaccinates alone, though not to the same degree.

Protection from lethal challenge was shown in all of the groups receiving IFN-I and NDV vaccine as shown in Table 5, but not in the PBS (negative) controls. One of the PBS controls demonstrated some degree of protection which may have been due to resistance by the broilers in that treatment group, or a small degree of contamination in that treatment group. It should be noted that there was 100% protection in all other treatment groups. Although protection was also observed in birds that received viral vaccine without IFN-I in ovo, the viral vaccine was not safe unless co-administered with IFN-I.

These data generated in maternal antibody positive broilers, indicate vaccination with NDV and IFN-I in ovo is safe and efficacious.

TABLE 5

| Treatment replicate group # | % Protected |
|---|---|
| 1--PBS | 41.7% |
| 1a-PBS | 8.3 |
| 2--$10^{2.5}$B1 LaSota, 30 μg IFN-I | 100 |
| 2a--$10^{2.5}$B1 LaSota, 30 μg IFN-I | 100 |
| 3--$10^{2.5}$B1 LaSota, 20 μg IFN-I | 100 |
| 3a--$10^{2.5}$B1 LaSota, 20 μg IFN-I | 100 |
| 4--$10^{2.5}$B1 LaSota, 10 μg IFN-I | 100 |
| 4a--$10^{2.5}$B1 LaSota, 10 μg IFN-I | 100 |
| 5--$10^{3.5}$B1 LaSota, 20 μg IFN-I | 100 |
| 5a--$10^{3.5}$B1 LaSota, 20 μg IFN-I | 100 |
| 6--$10^{2.5}$B1 LaSota | 100 |
| 6a--$10^{2.5}$B1 LaSota | 100 |
| 7--$10^{3.5}$B1 LaSota | not tested |
| 7a--$10^{3.5}$B1 LaSota | not tested |

EXAMPLE 16

Vaccination of Commercial Broilers with IFN-NDV

Safety and dose-response studies are carried out as described above to determine the optimal (i.e., safe and efficacious) doses of both NDV vaccine and IFN-I in maternal antibody positive broilers. Commercial broilers (Cobb×Cobb) are divided into treatment groups that receive PBS or vaccine and/or IFN-I by subcutaneous injection at various times post-hatch (e.g., 1, 3, 7, 10 days). For ease of handling, it is preferred to administer IFN-NDV at the time the birds are transferred from the hatcher, typically, one or two days after hatch. All birds are screened for the presence of anti-NDV antibodies, by any method known in the art, before the start of the study. Non-vaccinated control birds are isolated from vaccinated birds during the course of the study to prevent infection by virus shedding from the vaccinated birds.

Additional studies are undertaken to follow the time course of maternal antibody disappearance (i.e., antibodies against NDV) after hatch.

After optimal doses of both vaccine and IFN-I have been identified, an efficacy study is carried out as described in Example 12 and Example 14, with the exception that vaccination is post-hatch. Challenge NDV is administered after the time when passive immunity from maternal antibodies has substantially or completely disappeared. Maternal antibody positive birds administered IFN-NDV demonstrate substantially improved resistance to a virulent NDV challenge as compared with birds treated with PBS (controls), NDV or IFN alone.

Although the foregoing invention has been described in some detail by way of illustration and example for purposes of clarity and understanding, it will be obvious that certain changes and modifications may be practiced within the scope of the appended claims.

That which is claimed is:

1. A method of producing protective immunity against a viral disease in an avian subject, comprising:

(a) administering to an avian subject in ovo a composition comprising a vaccine comprising a live pathogenic virus; and (b) administering to the avian subject in ovo a composition comprising interferon;

wherein the live pathogenic virus is administered in an amount effective to produce an immune response in the avian subject; and wherein the interferon is administered in an amount effective to (1) reduce the pathology that would occur in the absence of the interferon due to the administration of the vaccine, and (2) allow the production of a protective immune response in the avian subject.

2. The method according to claim 1, wherein the interferon is a Type I interferon.

3. The method according to claim 2, wherein the Type I interferon is a chicken Type I interferon.

4. The method according to claim 1, wherein said administering steps are carried out during the last half of in ovo incubation.

5. The method according to claim 1, wherein said administering steps are carried out during the last quarter of in ovo incubation.

6. The method according to claim 1, wherein said administering steps are carried out essentially concurrently.

7. The method according to claim 6, wherein the vaccine and the interferon are included in the same composition.

8. The method according to claim 1, wherein said administering steps are carried out by injection into the amnion of the egg.

9. The method according to claim 1, wherein the live pathogenic virus is selected from the group consisting of rous sarcoma virus, Newcastle disease virus, infectious bursal disease virus, infectious bronchitis virus, avian infectious laryngeotracheitis virus, turkey rhinotracheitis virus, avian leukosis virus, Marek's disease virus, chicken anemia virus, avian influenza virus, Paramyxovirus group 2–9 viruses (PMV 2–9), avipox, herpes virus of turkeys, duck enteritis virus, Pacheco's disease, duck hepatitis virus, adenovirus, parvovirus, polyomavirus, pneumovirus, orthomyxovirus, coranovirus, reovirus, rotavirus, birnavirus, enterovirus, oncornavirus, arbovirus, flavovirus, and astrovirus.

10. The method according to claim 1, wherein the live pathogenic virus is a Newcastle disease virus.

11. The method according to claim 1, wherein the avian subject is administered about a $10^{-2}$ $EID_{50}$ to about a $10^6$ $EID_{50}$ dose of the live pathogenic virus.

12. The method according to claim 1, wherein the avian subject is selected from the group consisting of chickens, turkeys, ducks, geese, quail and pheasant.

13. The method according to claim 1, wherein the avian subject is a chicken.

14. The method according to claim 1, wherein the avian subject has maternal antibodies that recognize the live pathogenic virus.

15. A method of producing protective immunity against Newcastle disease in a chicken, comprising:
  (a) administering to a chicken during the last half of in ovo incubation a composition comprising a vaccine comprising a live pathogenic Newcastle disease virus; and
  (b) administering to a chicken during the last half of in ovo incubation a composition comprising a Type I interferon;
  wherein the live pathogenic virus is administered in an amount effective to produce an immune response in the chicken; and
  wherein the Type I interferon is administered in an amount effective to (1) reduce the pathology that would occur in the absence of the Type I interferon due to the administration of the vaccine, and (2) allow the production of a protective immune response in the chicken.

16. A method of reducing mortality from the administration of a live vaccine virus in ovo to an avian subject, comprising:
  (a) administering to an avian subject in ovo a composition comprising a vaccine comprising a live vaccine virus; and
  (b) administering to the avian subject in ovo a composition comprising interferon;
  wherein the live vaccine virus is administered in an amount effective to produce an immune response in the avian subject; and
  wherein the interferon is administered in an amount effective to (1) reduce the pathology that would occur in the absence of the interferon due to the administration of the vaccine, and (2) allow the production of a protective immune response in the avian subject.

17. The method according to claim 16, wherein the interferon is a Type I interferon.

18. The method according to claim 17, wherein the Type I interferon is a chicken Type I interferon.

19. The method according to claim 16, wherein said administering steps are carried out during the last quarter of in ovo incubation.

20. The method according to claim 16, wherein the vaccine and the Type I interferon are included in the same composition.

21. The method according to claim 16, wherein the live pathogenic virus is selected from the group consisting of rous sarcoma virus, Newcastle disease virus, infectious bursal disease virus, infectious bronchitis virus, avian infectious laryngeotracheitis virus, turkey rhinotracheitis virus, avian leukosis virus, Marek's disease virus, chicken anemia virus, avian influenza virus, Paramyxovirus group 2–9 viruses (PMV 2–9), avipox, herpes virus of turkeys, duck enteritis virus, Pacheco's disease, duck hepatitis virus, adenovirus, parvovirus, polyomavirus, pneumovirus, orthomyxovirus, coranovirus, reovirus, rotavirus, birnavirus, enterovirus, oncornavirus, arbovirus, flavovirus, and astrovirus.

22. The method according to claim 16, wherein the live pathogenic virus is a Newcastle disease virus.

23. The method according to claim 16, wherein the avian subject is administered about a $10^{-2}$ $EID_{50}$ to about a $10^6$ $EID_{50}$ dose of the live pathogenic virus.

24. The method according to claim 16, wherein the avian subject is selected from the group consisting of chickens, turkeys, ducks, geese, quail and pheasant.

25. The method according to claim 16, wherein the avian subject is a chicken.

26. The method according to claim 16, wherein the avian subject has maternal antibodies that recognize the live pathogenic virus.

27. A method of producing protective immunity against a viral disease in an avian subject, comprising:
  (a) administering to an avian subject in ovo a composition comprising a vaccine comprising a live pathogenic virus; and
  (b) administering to the avian subject in ovo a composition comprising about 1 µg to about 80 µg of a Type I interferon, said Type I interferon having a specific activity of $1\times10^5$ to $1\times10^8$ units per milligram;
  wherein the live pathogenic virus is administered in an amount effective to produce an immune response in the avian subject; and
  wherein the interferon is administered in an amount effective to (1) reduce the pathology that would occur in the absence of the interferon due to the administration of the vaccine, and (2) allow the production of a protective immune response in the avian subject.

28. The method according to claim 27, wherein the avian subject is administered about 10 µg to about 40 µg of the Type I interferon.

29. A method of reducing mortality from the administration of a live vaccine virus in ovo to an avian subject, comprising:
  (a) administering to an avian subject in ovo a composition comprising a vaccine comprising a live vaccine virus; and
  (b) administering to the avian subject in ovo a composition comprising about 10 µg to about 40 µg of a Type I interferon, said Type I interferon having a specific activity of $1\times10^5$ to $1\times10^8$ units per milligram;
  wherein the live vaccine virus is administered in an amount effective to produce an immune response in the avian subject and an amount effective to produce mortality in the absence of the interferon; and
  wherein the interferon is administered in an amount effective to (1) reduce the pathology that would occur in the absence of the interferon due to the administration of the vaccine, and (2) allow the production of a protective immune response in the avian subject.

30. The method according to claim 27, wherein the Type I interferon is a chicken Type I interferon.

31. The method according to claim 27, wherein said administering steps are carried out during the last half of in ovo incubation.

32. The method according to claim 27, wherein said administering steps are carried out during the last quarter of in ovo incubation.

33. The method according to claim 27, wherein said administering steps are carried out essentially concurrently.

34. The method according to claim 33, wherein the vaccine and the interferon are included in the same composition.

35. The method according to claim 27, wherein said administering steps are carried out by injection into the amnion of the egg.

36. The method according to claim 27, wherein the live pathogenic virus is selected from the group consisting of rous sarcoma virus, Newcastle disease virus, infectious bursal disease virus, infectious bronchitis virus, avian infectious laryngeotracheitis virus, turkey rhinotracheitis virus, avian leukosis virus, Marek's disease virus, chicken anemia virus, avian influenza virus, Paramyxovirus group 2–9 viruses (PMV 2–9), avipox, herpes virus of turkeys, duck enteritis virus, Pacheco's disease, duck hepatitis virus, adenovirus, parvovirus, polyomavirus, pneumovirus, orthomyxovirus, coranovirus, reovirus, rotavirus, birnavirus, enterovirus, oncornavirus, arbovirus, flavovirus, and astrovirus.

37. The method according to claim 27, wherein the live pathogenic virus is a Newcastle disease virus.

38. The method according to claim 27, wherein the avian subject is administered about a $10^{-2}$ $EID_{50}$ to about a $10^6$ $EID_{50}$ dose of the live pathogenic virus.

39. The method according to claim 27, wherein the avian subject is selected from the group consisting of chickens, turkeys, ducks, geese, quail and pheasant.

40. The method according to claim 27, wherein the avian subject is a chicken.

41. The method according to claim 27, wherein the avian subject has maternal antibodies that recognize the live pathogenic virus.

42. A method of producing protective immunity against Newcastle disease in a chicken, comprising:

(a) administering to a chicken during the last half of in ovo incubation a composition comprising a vaccine comprising about a $10^{-2}$ $EID_{50}$to about a $10^6$ $EID_{50}$ dose of a live pathogenic Newcastle disease virus; and (b) administering to a chicken during the last half of in ovo incubation a composition about 10 $\mu$g to about 40 $\mu$g of a Type I interferon, said Type I interferon having a specific activity of $1\times10^5$ to $1\times10^8$ units per milligram;

wherein the live pathogenic virus is administered in an amount effective to produce an immune response in the chicken; and wherein the Type I interferon is administered in an amount effective to (1) reduce the pathology that would occur in the absence of the Type I interferon due to the administration of the vaccine, and (2) allow the production of a protective immune response in the chicken.

43. A method of producing protective immunity against a pathogenic viral disease in an avian subject, comprising:

(a) administering to an avian subject in ovo a composition comprising a vaccine comprising a live pathogenic virus; and (b) administering to the avian subject in ovo a composition comprising interferon;

wherein the live pathogenic virus is administered in an amount effective to produce an immune response in the avian subject and in an amount sufficient to cause at least about a 30% decrease in hatch rate in specific pathogen free avian subjects in the absence of the interferon; and wherein the interferon is administered in an amount effective to (1) reduce the pathology that would occur in the absence of the interferon due to the administration of the vaccine, and (2) allow the production of a protective immune response in the avian subject.

* * * * *